US010675277B2

(12) United States Patent
Kárpáti et al.

(10) Patent No.: US 10,675,277 B2
(45) Date of Patent: *Jun. 9, 2020

(54) COMPLEXES OF IVACAFTOR AND ITS SALTS AND DERIVATIVES, PROCESS FOR THE PREPARATION THEREOF AND PHARMACEUTICAL COMPOSITIONS CONTAINING THEM

(71) Applicant: NanGenex Nanotechnology Incorporated, Budapest (HU)

(72) Inventors: Richárd Balázs Kárpáti, Tatabánya (HU); Gergo Patyi, Vecsés (HU); Orsolya Basa-Dénes, Eger (HU); Erzsébet Réka Angi, Nagykovácsi (HU); Tamás Jordán, Öcsöd (HU); Tamás Solymosi, Békéscsaba (HU); Hristos Glavinas, Szeged (HU); Genovéva Filipcsei, Budapest (HU)

(73) Assignee: NanGenex Nanotechnology Incorporated, Budapest (HU)

( * ) Notice: Subject to any disclaimer, the term of this patent is extended or adjusted under 35 U.S.C. 154(b) by 0 days.

This patent is subject to a terminal disclaimer.

(21) Appl. No.: 16/229,235

(22) Filed: Dec. 21, 2018

(65) Prior Publication Data

US 2019/0183877 A1    Jun. 20, 2019

Related U.S. Application Data

(62) Division of application No. 15/496,239, filed on Apr. 25, 2017, now Pat. No. 10,206,915.

(60) Provisional application No. 62/437,301, filed on Dec. 21, 2016, provisional application No. 62/327,133, filed on Apr. 25, 2016.

(51) Int. Cl.

| *A61K 31/47* | (2006.01) |
| *A61K 31/167* | (2006.01) |
| *A61K 31/136* | (2006.01) |
| *A61K 9/14* | (2006.01) |
| *A61K 9/16* | (2006.01) |
| *C07D 307/06* | (2006.01) |
| *G01N 21/552* | (2014.01) |
| *G01N 21/35* | (2014.01) |

(52) U.S. Cl.

CPC .............. *A61K 31/47* (2013.01); *A61K 9/14* (2013.01); *A61K 9/145* (2013.01); *A61K 9/146* (2013.01); *A61K 9/1617* (2013.01); *A61K 9/1635* (2013.01); *A61K 9/1641* (2013.01); *A61K 31/136* (2013.01); *A61K 31/167* (2013.01); *C07D 307/06* (2013.01); *G01N 21/552* (2013.01); *G01N 2021/3595* (2013.01)

(58) Field of Classification Search

CPC .... A61K 31/47; A61K 31/167; A61K 31/136; A61K 9/145; A61K 9/1617; A61K 9/1635; A61K 9/146; A61K 9/1641; A61K 9/14; C07D 307/06; G01N 21/552; G01N 202/3595

See application file for complete search history.

(56) References Cited

U.S. PATENT DOCUMENTS

| 6,969,529 B2 * | 11/2005 | Bosch ................... A61K 9/145 |
| | | 424/451 |
| 7,495,103 B2 | 2/2009 | Hadida-Ruah |
| 8,324,242 B2 | 12/2012 | Ruah |
| 8,354,427 B2 | 1/2013 | Van Goor |
| 8,507,534 B2 | 8/2013 | Keshavarz-Shokri |
| 8,653,103 B2 | 2/2014 | Keshavarz-Shokri |
| 8,716,338 B2 | 5/2014 | Young |
| 8,754,224 B2 | 6/2014 | Hurter |
| 8,846,718 B2 | 9/2014 | Keshavarz-Shokri |
| 8,993,600 B2 | 3/2015 | Hadida Ruah |
| 9,181,192 B2 | 11/2015 | Morgan |
| 10,206,915 B2 | 2/2019 | Kárpáti |
| 2013/0085158 A1 | 4/2013 | Keshavarz-Shokri |
| 2013/0296379 A1 | 11/2013 | Keshavarz-Shokri |
| 2014/0163068 A1 | 6/2014 | Verwijs |
| 2014/0221424 A1 | 8/2014 | Zha |
| 2014/0221430 A1 | 8/2014 | Keshavarz-Shokri |

(Continued)

FOREIGN PATENT DOCUMENTS

| CN | 104725314 | 6/2015 |
| EP | 2819670 | 1/2015 |

(Continued)

OTHER PUBLICATIONS

CoNCERT, Product Innovation. Patient Impact, Jeffries Healthcare Conference, Roger Tung, Ph.D., President and CEO, Jun. 3, 2015, 20 pages.

Morgan, A. et al., Design and Synthesis of Deuterated Analogs of Ivacaftor With Enhanced Pharmacokinetic Properties, CoNCERT Pharmaceuticals Inc., 2012, Poster, 1 page.

U.S. Appl. No. 15/496,239; Examiner Initiated Interview Summary dated Sep. 26, 2018; 1 page.

U.S. Appl. No. 15/496,239; Non-Final Office Action dated Jan. 30, 2018; 8 pages.

(Continued)

*Primary Examiner* — Shirley V Gembeh

(74) *Attorney, Agent, or Firm* — Dennis A. Bennett; Brock D. Levin; Lauren L. Stevens

(57) ABSTRACT

Disclosed herein are pharmaceutically acceptable complex formulations comprising complexes of Ivacaftor, or a salt or derivative thereof, together with complexation agents and pharmaceutically acceptable excipients; processes for the preparation thereof; and pharmaceutical compositions containing them. The complexes possess instantaneous redispersibility, increased apparent solubility and permeability compared to KALYDECO, no observable food effect which deliver the opportunity of precise dosing and ease of administration of the reconstituted complex Ivacaftor in solution form.

14 Claims, 18 Drawing Sheets

(56) References Cited

U.S. PATENT DOCUMENTS

| | | |
|---|---|---|
| 2014/0255483 A1 | 9/2014 | Dokou |
| 2015/0010628 A1 | 1/2015 | Dokou |
| 2015/0024047 A1 | 1/2015 | Dokou |
| 2015/0140094 A1 | 5/2015 | Verwijs |
| 2015/0182517 A1 | 7/2015 | Alargova |
| 2015/0196539 A1 | 7/2015 | Keshavarz-Shokri |
| 2015/0246031 A1 | 9/2015 | Dokou |
| 2016/0039800 A1 | 2/2016 | Young |
| 2017/0304287 A1 | 10/2017 | Kárpáti |

FOREIGN PATENT DOCUMENTS

| | | |
|---|---|---|
| EP | 2826776 | 1/2015 |
| EP | 2872122 | 5/2015 |
| JP | 2014097964 | 5/2014 |
| WO | 2009076141 | 6/2009 |
| WO | 2011127241 | 10/2011 |
| WO | 2011127290 | 10/2011 |
| WO | 2013112804 | 8/2013 |
| WO | 2014118805 | 8/2014 |
| WO | 2014125506 | 8/2014 |
| WO | 2014135096 | 9/2014 |
| WO | 2015070336 | 5/2015 |
| WO | 2015071836 | 5/2015 |
| WO | 2015073231 | 5/2015 |
| WO | 2015160787 | 10/2015 |
| WO | 2015175773 | 11/2015 |

OTHER PUBLICATIONS

U.S. Appl. No. 15/496,239; Notice of Allowance dated Sep. 26, 2018; 9 pages.

Uttamsingh, V. et al., CTP-656 Multiple Dose Pharmacokinetic Profile Continues to Support a Once-Daily Potentiator for Cystic Fibrosis Patients With Gating Mutations, CoNCERT Pharmaceuticals, Inc., #224, Poster, 1 page.

* cited by examiner

Fig. 1

| | | Pharmaceutically acceptable excipient | | | | | | | | | | | |
|---|---|---|---|---|---|---|---|---|---|---|---|---|---|
| | | Citric Acid | Cetylpyridinium chloride | D-Mannitol | Dioctyl sodium sulfosuccinate | Kollicoat-IR | Poloxamer (Lutrol F127) | Meglumine | Sodium Acetate | NONE | Sodium deoxycolate | Sodium-lauryl-sulfate | Solutol HS15 | Lactose |
| Complexation agent | Gelucire 44/14 | - | + | - | - | - | - | - | - | - | + | - | - |
| | Gelucire 50/13 | - | + | - | - | - | - | - | - | - | - | - | - |
| | Klucell EF | - | + | - | - | - | + | - | - | - | - | - | - |
| | Poloxamer (Lutrol F127) | - | + | - | + | - | + | - | + | - | - | + | - | - |
| | Kollidon VA64 | - | + | + | + | + | + | + | + | + | + | + | - | + |
| | PEOX50 | - | + | - | - | - | - | - | - | - | - | - | - |
| | PEOX500 | - | + | - | - | - | - | - | - | - | - | - | - |
| | Plasdone K-12 | - | + | + | + | - | - | + | - | + | + | + | - | + |
| | PMAMVE | - | - | - | - | + | + | - | - | - | - | - | - |
| | PVP 40 | - | + | - | + | - | - | - | - | - | - | + | - | - |
| | PVP K90 | - | + | - | + | - | - | - | - | - | - | + | - | - |
| | PVP 10 | - | + | - | + | - | - | - | - | - | - | + | - | - |
| | Soluplus | - | + | - | - | - | - | - | - | - | - | - | - |
| | Tetronic 1107 | - | + | - | + | - | + | - | - | - | + | + | - | - |
| | TPGS | + | + | + | + | - | + | - | + | + | + | - | + |
| + redispersable solid Ivacaftor complex in ultrapurified water | | | | | | | | | | | | | | |
| - non-redispersable solid Ivacaftor complex in ultrapurified water | | | | | | | | | | | | | | |

Fig. 2

| Complexation agent | Pharmaceutically acceptable excipient | Redispersibility | PAMPA permability ($\times 10^{-6}$ cm/s) |
|---|---|---|---|
| Kollidon VA64 | Sodium lauryl sulfate | + | 0.432 |
| Kollidon VA64 | Sodium deoxycolate | + | 0.3767 |
| Kollidon VA64 | Cetylpyridinium chloride | + | 0.3522 |
| Poloxamer (Pluronic PE10500) | Cetylpyridinium chloride | + | 0.3422 |
| Tetronic | Sodium deoxycholate | + | 0.3147 |
| d-alpha tocopheryl polyethylene glycol 1000 succinate | Poloxamer (Pluronic PE10500) | + | 0.312 |
| Poloxamer (Pluronic PE10500) | Sodium-lauryl-sulfate | + | 0.2764 |
| Poloxamer (Pluronic PE10500) | Dioctyl sodium sulfosuccinate | + | 0.2688 |
| d-alpha tocopheryl polyethylene glycol 1000 succinate | Citric Acid | + | 0.2686 |
| d-alpha tocopheryl polyethylene glycol 1000 succinate | Poloxamer (Lutrol F127) | + | 0.2544 |
| d-alpha tocopheryl polyethylene glycol 1000 succinate | Sodium-lauryl-sulfate | + | 0.2456 |
| Gelucire 44/14 | Cetylpyridinium chloride | + | 0.2324 |
| Poloxamer (Lutrol F127) | Cetylpyridinium chloride | + | 0.2127 |
| d-alpha tocopheryl polyethylene glycol 1000 succinate | Cetylpyridinium chloride | + | 0.1492 |
| Kollidon VA64 | Sodium deoxycholate | + | 0.1196 |
| Kollidon VA64 | Meglumine | + | 0.085 |
| Plasdone K-12 | D-Mannitol | + | 0.0565 |
| Kollidon VA64 | Sodium acetate | + | 0.0534 |

*Mass ratio of API:complexation agent:pharmaceutically acceptable excipient = 1:2:1*

Fig. 3

| Mass ratio of API:complexation agent:poloxamer:pharmaceutically acceptable excipient | Redispersibility in UP water | PAMPA permeability (water) ($\times 10^{-6}$ cm/s) |
|---|---|---|
| 1 : 3 : 2 : 1 | + | 0.656 |
| 1 : 3 : 2 : 0.8 | + | 0.146 |
| 1 : 3 : 2 : 0.6 | + | 0.255 |
| 1 : 2.5 : 2.5 : 1 | + | 0.239 |
| 1 : 2.5 : 2.5 : 0.6 | + | 0.21 |
| 1 : 3 : 1 : 1 | - | not measured |
| 1 : 3 : 1 : 0.6 | - | not measured |
| 1 : 4 : 1 : 1 | - | not measured |

Lyophilised samples

Fig. 4

| Lyophilised samples | | | |
|---|---|---|---|
| Mass ratio of API:complexation agent:poloxamer:pharmaceutically acceptable excipient = 1 : 3 : 2 : 1 | Poloxamer type | Redispersibility in UP water | PAMPA permeability (water) ($\times 10^{-6}$ cm/s) |
| | Pluronic F108 (Poloxamer 338) | + | 0.846 |
| | Lutrol F127 (Poloxamer 407) | + | 0.376 |
| | Pluronic PE 6800 (Poloxamer 188) | - | 0.353 |
| | Pluronic PE 10500 | + | 0.389 |
| Spray-dryed samples | | | |
| Mass ratio of API:complexation agent:poloxamer:pharmaceutically acceptable excipient = 1 : 3 : 2 : 1 | Pluronic F108 (Poloxamer 338) | + | 0.815 |
| | Lutrol F127 (Poloxamer 407) | + | 0.743 |
| Mass ratio of API:complexation agent:pharmaceutically acceptable excipient = 1 : 6 : 3 | None | + | 0.459 |

Fig. 5

| Composition | Solution 1 : Solution 2 ratio | Appearance |
|---|---|---|
| Mass ratio of API/complexation agent/poloxamer/pharmaceutically acceptable excipient = 1 : 3 : 2 : 1 | 1:1 | clear colloid solution, stable for 4 h |
| | 1:2 | slightly opalescent, stable for 4 mins |
| | 1:3 | slightly opalescent, stable for 4 mins |
| | 1:4 | slightly opalescent, stable for 4 mins |

Fig. 6

| Composition | Solution 1 (S): Solution 2 (AS) ratio | Vs, V$_{AS}$ (mL/min) | T (°C) | Appearance |
|---|---|---|---|---|
| Mass ratio of API/complexation agent/poloxamer 338/pharmaceutically acceptable excipient = 1 : 3 : 2 : 1 | 1:1 | 2.5 | 25 | Inhomogeneous solution |
| | | 5 | 25 | Inhomogeneous solution |
| | | 10 | 25 | Inhomogeneous solution |
| | | 20 | 25 | Inhomogeneous solution |
| | | 30 | 25 | Inhomogeneous solution |
| | | 40 | 25 | Homogeneous colloid solution |
| | | 20 | 40 | Inhomogeneous solution |
| | | 30 | 40 | Inhomogeneous solution |
| | | 40 | 40 | Homogeneous colloid solution |
| | | 40 | 20 | Homogeneous colloid solution |
| | | 40 | 30 | Homogeneous colloid solution |
| | | 40 | 50 | Inhomogeneous solution |

Fig. 7

| Time (min) | Dissolved Ivacaftor (%) |
| --- | --- |
| 0 | 0 |
| 5 | 57.23% |
| 10 | 96.72% |
| 15 | 94.99% |
| 20 | 95.59% |
| 30 | 96.48% |
| 45 | 99.76% |
| 60 | 95.59% |

Fig. 8

| Composition | PAMPA permeability (x10$^{-6}$ cm/s) | | |
|---|---|---|---|
| | Water | FaSSIF | FeSSIF |
| Crystalline Ivacaftor | 0.038 | 0.029 | 0.063 |
| Complex Ivacaftor formulation containing Kollidon VA 64, poloxamer (Poloxamer 338 – Pluronic F108) and sodium lauryl sulfate | 0.815 | 0.680 | 0.826 |
| Complex Ivacaftor formulation containing Kollidon VA 64, poloxamer (poloxamer 407- Lutrol F127) and sodium lauryl sulfate [API/Kollidon VA 64/Poloxamer 407/SDS = 1/3/2/2 (w/w)] | 0.743 | 0.626 | 0.692 |
| Complex Ivacaftor formulation containing Kollidon VA 64, poloxamer (poloxamer 407- Lutrol F127) and sodium-lauryl-sulfate [API/Kollidon VA 64/Poloxamer 407/SDS = 1/3/0.6/0.6 (w/w)] | 0.871 | 0.454 | 0.624 |
| Complex Ivacaftor formulation containing Kollidon VA 64 and sodium lauryl sulfate | 0.459 | 0.528 | 0.664 |

Fig. 9

| Composition | Storage condition | Time (month) | Medium | PAMPA permeability (x10⁻⁶ cm/s) |
|---|---|---|---|---|
| Complex Ivacaftor formulation containing Kollidon VA 64, poloxamer (Poloxamer 338 – Pluronic F108) and sodium lauryl sulfate | 40°C | 18 | Water | 0.468 |
| | | | FaSSIF | 0.479 |
| | | | FeSSIF | 0.450 |
| Complex Ivacaftor formulation containing Kollidon VA 64, poloxamer (poloxamer 407 - Lutrol F127) and sodium lauryl sulfate  Ivacaftor:Kollidon VA 64:Poloxamer 407: sodium lauryl sulfate = 1:3:2:2 (w/w) | RT | 6 | Water | 0.515 |
| | | | FaSSIF | 0.468 |
| | | | FeSSIF | 0.577 |
| Complex Ivacaftor formulation containing Kollidon VA 64, poloxamer (poloxamer 407 - Lutrol F127) and sodium lauryl sulfate  Ivacaftor:Kollidon VA 64:Poloxamer 407: sodium lauryl sulfate = 1:3:0.6:0.6 (w/w) | RT | 6 | Water | 0.472 |
| | | | FaSSIF | 0.448 |
| | | | FeSSIF | 0.505 |
| Complex Ivacaftor formulation containing Luviskol VA 64 and sodium-lauryl-sulfate | 40°C | 20 | Water | 0.506 |
| | | | FaSSIF | 0.468 |
| | | | FeSSIF | 0.577 |

Fig. 15

| Composition | Ivacaftor content of the dispersions (mg/mL) | Apparent solubility (mg/mL) |
|---|---|---|
| Crystalline Ivacaftor | 1 | 0 |
| Physical mixture of Ivacaftor, Kollidon VA 64, poloxamer (Poloxamer 338 - Pluronic F108) and sodium lauryl sulfate | 3 | 0.043 |
| Crystalline Ivacaftor in 3 mg/mL sodium lauryl sulfate aqueous solution | 3 | 0.017 |
| Amorphous Ivacaftor in 3 mg/mL sodium lauryl sulfate aqueous solution | 3 | 0.077 |
| Solid dispersion | 1 | 0.071 |
| Complex Ivacaftor formulation containing Kollidon VA 64, poloxamer (Poloxamer 338 - Pluronic F108) and sodium lauryl sulfate | 1 | 0.991 |
| Complex Ivacaftor formulation containing Kollidon VA 64, poloxamer (Poloxamer 338 - Pluronic F108) and sodium lauryl sulfate | 10 | 9.463 |
| Complex Ivacaftor formulation containing Kollidon VA 64, poloxamer (Poloxamer 407 – Lutrol F127) and sodium lauryl sulfate | 1 | 0.944 |
| Complex Ivacaftor formulation containing Kollidon VA 64, and sodium lauryl sulfate | 1 | 0.936 |

Fig. 18

| Test item | | Feeding condition | $C_{max}$(ng/ml) | $C_{24h}$(ng/ml) | AUC (ng/ml*h) |
|---|---|---|---|---|---|
| Complex formulation | Ivacaftor | fed | 1620 ± 405 | 1230 ± 364 | 41652 ± 11758 |
| Complex formulation | Ivacaftor | fasted | 1955 ± 359 | 1050 ± 86 | 36728 ± 4947 |
| Literature reference data* | | fasted | 2255 ± 748 | 774 ± 230 | 29448 ± 8464 |

*http://www.concertpharma.com/news/documents/ISSX2013DIvacaftor.pdf

COMPLEXES OF IVACAFTOR AND ITS SALTS AND DERIVATIVES, PROCESS FOR THE PREPARATION THEREOF AND PHARMACEUTICAL COMPOSITIONS CONTAINING THEM

This application is a division of U.S. patent application Ser. No. 15/496,239, filed Apr. 25, 2017, which claims the benefit of priority to U.S. Provisional Application Nos. 62/327,133, filed Apr. 25, 2016, and 62/437,301, filed Dec. 21, 2016, the disclosures of which are hereby incorporated by reference as if written herein in their entireties.

FIELD OF THE INVENTION

Disclosed herein are stable complexes with controlled particle size, increased apparent solubility and increased dissolution rate compared to KALYDECO comprising as active compound Ivacaftor, or its salts, or derivatives thereof, which is useful in the treatment of cystic fibrosis transmembrane conductance regulator (CFTR) mediated disease. More specifically, the complexes possess instantaneous redispersibility, increased apparent solubility and permeability, no observable food effect which deliver the opportunity of precise dosing and ease of administration of the reconstituted complex in solution form. Further disclosed are methods of formulating and manufacturing said complexes, pharmaceutical compositions containing said complexes, and uses and methods of treatment using the complex and its compositions.

BACKGROUND OF THE INVENTION

The active ingredient in KALYDECO tablets is Ivacaftor, which has the following chemical name: N-(2,4-di-tert-butyl-5-hydroxyphenyl)-1,4-dihydro-4-oxoquinoline-3-carboxamide. Its molecular formula is $C_{24}H_{28}N_2O_3$ and its molecular weight is 392.49. Ivacaftor has the following structural formula:

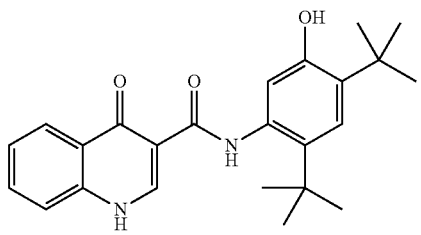 [SMILES: CC(C)(C)c1cc(C(C)(C)C)c(NC(=O)c2c[nH]c3ccccc3c2=O)cc1O]

Ivacaftor is a white to off-white powder that is practically insoluble in water (<0.05 microgram/mL). Due to poor aqueous solubility, extensive formulation efforts were required and resulted in a spray-dried dispersion of Ivacaftor suitable for oral administration. KALYDECO containing the spray-dried dispersion of Ivacaftor is available as a light blue capsule-shaped, film-coated tablet for oral administration containing 150 mg of Ivacaftor. Each tablet contains the inactive ingredients colloidal silicon dioxide, croscarmellose sodium, hypromellose acetate succinate, lactose monohydrate, magnesium stearate, microcrystalline cellulose, and sodium lauryl sulfate. The tablet film coat contains carnauba wax, FD&C Blue #2, PEG 3350, polyvinyl alcohol, talc, and titanium dioxide. The printing ink contains ammonium hydroxide, iron oxide black, propylene glycol, and shellac.

Ivacaftor is a potentiator of the CFTR protein. The CFTR protein is a chloride channel present at the surface of epithelial cells in multiple organs. Ivacaftor facilitates increased chloride transport by potentiating the channel-open probability (or gating) of the CFTR protein.

After oral administration of a single 150 mg dose to healthy volunteers in a fed state, peak plasma concentrations ($t_{max}$) occurred at approximately 4 hours, and the mean (±SD) for AUC and $C_{max}$ were 10,600 (5260) ng*hr/mL and 768 (233) ng/mL, respectively. After every 12-hour dosing, steady-state plasma concentrations of Ivacaftor were reached by days 3 to 5, with an accumulation ratio ranging from 2.2 to 2.9.

The exposure of Ivacaftor increased approximately 2- to 4-fold when given with food containing fat. Therefore, KALYDECO should be administered with fat-containing food.

Examples of fat-containing foods include eggs, butter, peanut butter, and cheese pizza. The median (range) $t_{max}$ is approximately 4.0 (3.0; 6.0) hours in the fed state.

The mean apparent volume of distribution (Vz/F) of Ivacaftor after a single dose of 275 mg of KALYDECO in the fed state was similar for healthy subjects and patients with CF. After oral administration of 150 mg every 12 hours for 7 days to healthy volunteers in a fed state, the mean (±SD) for apparent volume of distribution was 353 (122) L.

Ivacaftor is extensively metabolized in humans. In-vitro and clinical studies indicate that Ivacaftor is primarily metabolized by CYP3A. M1 and M6 are the two major metabolites of Ivacaftor in humans. M1 has approximately one-sixth the potency of Ivacaftor and is considered pharmacologically active. M6 has less than one-fiftieth the potency of Ivacaftor and is not considered pharmacologically active.

Following oral administration, the majority of Ivacaftor (87.8%) is eliminated in the feces after metabolic conversion. The major metabolites M1 and M6 accounted for approximately 65% of the total dose eliminated with 22% as M1 and 43% as M6. There was negligible urinary excretion of Ivacaftor as unchanged parent. The apparent terminal half-life was approximately 12 hours following a single dose. The mean apparent clearance (CL/F) of Ivacaftor was similar for healthy subjects and patients with CF. The CL/F (SD) for the 150 mg dose was 17.3 (8.4) L/hr in healthy subjects.

The main pharmacokinetic problem associated with the oral delivery of Ivacaftor is a significant positive food effect which renders the current tablet formulation to be taken with a high fat meal which results in variability of exposure and does not allow the precise dosing of the compound.

In order to overcome the problems associated with prior conventional Ivacaftor formulations and available drug delivery systems, novel complex formulations of Ivacaftor and salts or derivatives thereof together with complexation agents and pharmaceutically acceptable excipients were prepared. The novel complexes possess instantaneous redispersibility, increased apparent solubility and permeability compared to KALYDECO, no observable food effect which deliver the opportunity of precise dosing and ease of administration of the reconstituted complex in solution form.

BRIEF DESCRIPTION OF THE INVENTION

Disclosed herein is a stable complex with improved physicochemical characteristics and enhanced biological performance comprising
  i. Ivacaftor, or a salt or derivatives thereof;
  ii. at least one complexation agent chosen from polyethylene glycol glycerides composed of mono-, di- and triglycerides and mono- and diesters of polyethylene glycol, hydroxypropylcellulose, poloxamers (copolymers of ethylene oxide and propylene oxide blocks), copolymers of vinylpyrrolidone and vinyl acetate copolymer, poly(2-ethyl-2-oxazoline), polyvinylpyrrolidone, poly(maleic acid/methyl vinyl ether), polyvinyl caprolactam-polyvinyl acetate-polyethylene glycol graft copolymer, ethylene oxide/propylene oxide tetra functional block copolymer, and d-alpha tocopheryl polyethylene glycol 1000 succinate; and
  iii. optionally, one or more pharmaceutically acceptable excipients;
wherein said complex has a particle size is between 10 nm and 600 nm, and possesses one or more among the following features:
  a) is instantaneously redispersible in physiological relevant media;
  b) is stable in solid form and in colloid solution and/or dispersion;
  c) has an apparent solubility in water is of at least 1 mg/mL;
  d) has a PAMPA permeability of at least $0.4 \times 10^{-6}$ cm/s when dispersed in distilled water, which does not decrease in time at least for 6 months; and
  e) exhibits no observable food effect.

In an embodiment, said complex has a particle size in the range between 10 nm and 400 nm.

In an embodiment, said complex exhibits X-ray amorphous character in the solid form.

In an embodiment, said complex possesses at least two of the properties described in a)-e).

In an embodiment, said complex possesses at least three of the properties described in a)-e).

In an embodiment, said complex possesses instantaneous redispersibility, has an apparent solubility in water of at least 1 mg/mL, exhibits no observable food effect which deliver the opportunity of precise dosing and ease of administration of the reconstituted complex Ivacaftor in solution form.

In an embodiment, said complex possesses instantaneous redispersibility, has a PAMPA permeability of at least $0.4 \times 10^{-6}$ cm/s when dispersed in water, FaSSIF or FeSSIF biorelevant media, which does not decrease in time at least for 6 month, exhibits no observable food effect which deliver the opportunity of precise dosing and ease of administration of the reconstituted complex Ivacaftor in solution form.

In an embodiment, said complex has an apparent solubility in water of at least 1 mg/mL and a PAMPA permeability of at least $0.5 \times 10^{-6}$ cm/s.

In an embodiment, said complex possesses instantaneous redispersibility, has an apparent solubility in water of at least 1 mg/mL, and has a PAMPA permeability of at least $0.5 \times 10^{-6}$ cm/s.

In an embodiment, said complexation agent is selected from the group consisting of copolymers of vinylpyrrolidone and vinylacetate and poloxamers.

In an embodiment, said complexation agent is a copolymer of vinylpyrrolidone and vinylacetate.

In an embodiment, said pharmaceutically acceptable excipient is chosen from sodium deoxycolate, dioctyl sodium sulfosuccinate, sodium acetate, cetylpyridinium chloride, citric acid, meglumine and sodium lauryl sulfate.

In an embodiment, said pharmaceutically acceptable excipient is sodium lauryl sulfate.

The complex according to Point 1 comprising
  a) Ivacaftor;
  b) a complexation agent which is a copolymer of vinylpyrrolidone and vinylacetate; and
  c) a pharmaceutically acceptable excipient which is sodium lauryl sulfate;
wherein said complex is characterized by infrared (ATR) spectrum having characteristic peaks at 588 $cm^{-1}$, 628 $cm^{-1}$, 767 $cm^{-1}$, 842 $cm^{-1}$, 962 $cm^{-1}$, 1019 $cm^{-1}$, 1108 $cm^{-1}$, 1148 $cm^{-1}$, 1240 $cm^{-1}$, 1343 $cm^{-1}$, 1370 $cm^{-1}$, 1425 $cm^{-1}$, 1465 $cm^{-1}$, 1525 $cm^{-1}$, 1567 $cm^{-1}$, 1666 $cm^{-1}$ and 1732 $cm^{-1}$; and
is characterized by Raman shifts at 552 $cm^{-1}$, 648 $cm^{-1}$, 826 $cm^{-1}$, 845 $cm^{-1}$, 888 $cm^{-1}$, 932 $cm^{-1}$, 1026 $cm^{-1}$, 1062 $cm^{-1}$, 1082 $cm^{-1}$, 1129 $cm^{-1}$, 1140 $cm^{-1}$, 1208 $cm^{-1}$, 1233 $cm^{-1}$, 1262 $cm^{-1}$, 1284 $cm^{-1}$, 1295 $cm^{-1}$, 1361 $cm^{-1}$, 1450 $cm^{-1}$, 1528 $cm^{-1}$, 1573 $cm^{-1}$, 1618 $cm^{-1}$, 1677 $cm^{-1}$, 1738 $cm^{-1}$, 746 $cm^{-1}$, 2884 $cm^{-1}$ and 2936 $cm^{-1}$.

In an embodiment, said composition further comprises a poloxamer.

In an embodiment, said complexing agent which is a copolymer of vinylpyrrolidone and vinylacetate, and optionally a poloxamer, and pharmaceutically acceptable excipient which is sodium lauryl sulfate, are present in a total amount ranging from about 1.0 weight % to about 95.0 weight % based on the total weight of the complex.

In an embodiment, said complexation agent which is a copolymer of vinylpyrrolidone and vinylacetate, and optionally a poloxamer, and pharmaceutically acceptable excipient which is sodium lauryl sulfate, are present in a total amount ranging from about 50 weight % to about 95.0 weight % based on the total weight of the complex.

In an embodiment, said complex has an increased dissolution rate compared to KALYDECO.

Disclosed herein is a process for the preparation of said stable complex, said process comprising the step of mixing a solution of Ivacaftor, and at least one complexation agent which is a copolymer of vinylpyrrolidone and vinylacetate, and optionally a poloxamer, in a pharmaceutically acceptable solvent with an aqueous solution containing at least one pharmaceutically accepted excipient selected from the group of sodium deoxycholate, dioctyl sodium sulfosuccinate, sodium acetate, cetylpyridinium chloride, citric acid, meglumine and sodium lauryl sulfate.

In an embodiment, said process is performed in a continuous flow instrument.

In an embodiment, said continuous flow instrument is a microfluidic flow instrument.

In an embodiment, said pharmaceutically acceptable solvent is chosen from water, methanol, ethanol, isopropanol, n-propanol, acetone, acetonitrile, dimethyl-sulfoxide, tetrahydrofuran, or combinations thereof.

In an embodiment, said pharmaceutically acceptable solvent is tetrahydrofuran.

In an embodiment, said solvents are miscible with each other and the aqueous solvent comprises 0.1 to 99.9% weight of the final solution.

Disclosed herein is a pharmaceutical composition comprising said stable complex together with a pharmaceutically acceptable carrier.

In an embodiment, said composition is suitable for oral, pulmonary, rectal, colonic, parenteral, intracisternal, intravaginal, intraperitoneal, ocular, otic, local, buccal, nasal, or topical administration.

In an embodiment, said composition is suitable for oral administration.

In an embodiment, said pharmaceutical composition comprises the fast dissolving granules of the complex Ivacaftor formulation according to Point 1.

In an embodiment, said granules are suitable for the preparation of sachet dosage form.

Disclosed herein is said complex for use in the treatment of CFTR mediated diseases.

In an embodiment, said CFTR mediated disease is selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington's, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease, Osteoporosis, Osteopenia, bone healing and bone growth (including bone repair, bone regeneration, reducing bone resorption and increasing bone deposition), Gorham's Syndrome, chloride channelopathies such as myotonia congenita (Thomson and Becker forms), Bartter's syndrome type III, Dent's disease, hyperekplexia, epilepsy, lysosomal storage disease, Angelman syndrome, and Primary Ciliary Dyskinesia (PCD), a term for inherited disorders of the structure and/or function of cilia, including PCD with situs inversus (also known as Kartagener syndrome), PCD without situs inversus and ciliary aplasia.

Disclosed herein is a method of treatment of CFTR mediated diseases comprising administration of a therapeutically effective amount of said complex or said pharmaceutical composition.

Disclosed herein is a stable complex comprising
a) 5-40% by weight of Ivacaftor, or a salt or derivative thereof;
b) 20-80% by weight of a copolymer of vinylpyrrolidone and vinylacetate;
c) 5-40% by weight of sodium lauryl sulfate; and
d) optionally 0-50% by weight of a poloxamer;
wherein said complex has a controlled particle size in the range between 10 nm and 600 nm; and
wherein said complex is not obtained via a milling process, high pressure homogenization process, encapsulation process or solid dispersion processes.

In an embodiment, said complex further comprises one or more additional active agents.

In an embodiment, said additional active agent Lumacaftor, Tezacaftor or chosen from agents used for the treatment of CFTR mediated diseases.

DESCRIPTION OF THE INVENTION

Disclosed herein are stable complexes comprising as active compound Ivacaftor, or salts or derivatives thereof; and at least one complexation agent.

In an embodiment, said complex further comprises at least one pharmaceutically acceptable excipient.

We have found that only the selected combinations of complexation agents and pharmaceutically acceptable excipients result in stable complex formulations having improved physicochemical characteristics and enhanced biological performance compared to KALYDECO.

The complexing agents themselves or together with the pharmaceutically acceptable excipients have the function to form a complex structure with an active pharmaceutical ingredient through non-covalent secondary interactions. The secondary interactions can form through electrostatic interactions such as ionic interactions, H-bonding, dipole-dipole interactions, dipole-induced dipole interactions, London dispersion forces, $\pi$-$\pi$ interactions, and hydrophobic interactions.

In an embodiment, said stable complex with improved physicochemical characteristics and enhanced biological performance compared to KALYDECO comprising
i. Ivacaftor, or a salt therefor derivatives thereof;
ii. at least one complexation agent chosen from polyethylene glycol glycerides composed of mono-, di- and triglycerides and mono- and diesters of polyethylene glycol, hydroxypropylcellulose, poloxamers (copolymers of ethylene oxide and propylene oxide blocks), copolymers of vinylpyrrolidone and vinyl acetate copolymer, poly(2-ethyl-2-oxazoline), polyvinylpyrrolidone, poly(maleic acid/methyl vinyl ether), polyvinyl caprolactam-polyvinyl acetate-polyethylene glycol graft copolymer, ethylene oxide/propylene oxide tetra functional block copolymer, and d-alpha tocopheryl polyethylene glycol 1000 succinate; and
iii. optionally, pharmaceutically acceptable excipients;
wherein said complex has a particle size is between 10 nm and 600 nm, and possesses one or more among the following features:
a) is instantaneously redispersible in physiological relevant media;
b) is stable in solid form and in colloid solution and/or dispersion;
c) has an apparent solubility in water is of at least 1 mg/mL;
d) has a PAMPA permeability of at least 0.4×10-6 cm/s when dispersed in distilled water, which does not decrease in time at least for 6 months; and
e) exhibits no observable food effect.

In an embodiment, said complexing agent is chosen from polyethylene glycol glycerides composed of mono-, di- and triglycerides and mono- and diesters of polyethylene glycol, hydroxypropylcellulose, poloxamers (copolymers of ethylene oxide and propylene oxide blocks), copolymer of vinylpyrrolidone and vinyl acetate, poly(2-ethyl-2-oxazoline), polyvinylpyrrolidone, poly(maleic acid/methyl vinyl ether), (polyvinyl caprolactam-polyvinyl acetate-polyethylene glycol graft copolymer (e.g.; Soluplus), polyoxyl 15 hydroxystearate, ethylene oxide/propylene oxide tetra functional block copolymer, and d-alpha tocopheryl polyethylene glycol 1000 succinate.

In an embodiment, said complexation agent is chosen from copolymers of vinylpyrrolidone and vinyl acetate and poloxamers.

In an embodiment, said complexation agent is a copolymer of vinylpyrrolidone and vinyl acetate.

In an embodiment, said complexation agent is a poloxamer.

In an embodiment, said copolymer of vinylpyrrolidone and vinyl acetate has a 60:40 weight ratio of vinylpyrrolidone:vinyl acetate monomers.

In an embodiment, said poloxamer is poloxamer 338.

In an embodiment, said poloxamer is poloxamer 407.

In an embodiment, said pharmaceutically acceptable excipient is chosen from sodium lauryl sulfate (SDS), dioctyl sodium sulfosuccinate (DSS), cetylpyridinium chloride (CPC), sodium acetate (NaOAC), sodium deoxycolate (SDC), meglumine, D-mannitol, Kollicoat-IR, citric acid, and lactose.

In an embodiment, said pharmaceutically acceptable excipient is chosen from sodium deoxycolate, dioctyl sodium sulfosuccinate, sodium acetate, cetylpyridinium chloride, citric acid, meglumine and sodium lauryl sulfate.

In an embodiment, said pharmaceutically acceptable excipient is sodium lauryl sulfate.

In some embodiments, the compositions may additionally include one or more pharmaceutically acceptable excipients, auxiliary materials, carriers, active agents or combinations thereof.

In an embodiment said complex has a particle size in the range between 10 nm and 400 nm.

In an embodiment, said complex is instantaneously redispersible in physiological relevant media.

In an embodiment, said complex has increased dissolution rate compared to the commercially available form of Ivacaftor (KALYDECO®).

In an embodiment, said complex is stable in solid form and in colloid solution and/or dispersion.

In an embodiment, said complex has apparent solubility in water is at least 1 mg/mL.

In an embodiment, said complex exhibits X-ray amorphous character in the solid form.

In an embodiment, said complex has a PAMPA permeability of at least $0.4 \times 10^{-6}$ cm/s when dispersed in distilled water, which does not decrease in time at least for 6 months.

In an embodiment, the variability of exposure of the complex is significantly reduced compared to the commercially available form (KALYDECO®).

In an embodiment, said complex has no observable food effect, which allows the opportunity of precise dosing and ease of administration of the reconstituted complex in solution form.

In an embodiment said complex containing copolymer of vinylpyrrolidone and vinylacetate and poloxamer and sodium lauryl sulfate or its pharmaceutical composition characterized by the Raman spectrum shown in FIG. 11 and ATR spectrum shown in FIG. 12.

In an embodiment, said complex is characterized by characteristic Raman shifts at 552 cm$^{-1}$, 648 cm$^{-1}$, 826 cm$^{-1}$, 845 cm$^{-1}$, 888 cm$^{-1}$, 932 cm$^{-1}$, 1026 cm$^{-1}$, 1062 cm$^{-1}$, 1082 cm$^{-1}$, 1129 cm$^{-1}$, 1140 cm$^{-1}$, 1208 cm$^{-1}$, 1233 cm$^{-1}$, 1262 cm$^{-1}$, 1284 cm$^{-1}$, 1295 cm$^{-1}$, 1361 cm$^{-1}$, 1450 cm$^{-1}$, 1528 cm$^{-1}$, 1573 cm$^{-1}$, 1618 cm$^{-1}$, 1677 cm$^{-1}$, 1738 cm$^{-1}$, 746 cm$^{-1}$, 2884 cm$^{-1}$ and 2936 cm$^{-1}$.

In an embodiment, said complex is characterized by ATR spectrum having characteristic peaks at 588 cm$^{-1}$, 628 cm$^{-1}$, 767 cm$^{-1}$, 842 cm$^{-1}$, 962 cm$^{-1}$, 1019 cm$^{-1}$, 1108 cm$^{-1}$, 1148 cm$^{-1}$, 1240 cm$^{-1}$, 1343 cm$^{-1}$, 1370 cm$^{-1}$, 1425 cm$^{-1}$, 1465 cm$^{-1}$, 1525 cm$^{-1}$, 1567 cm$^{-1}$, 1666 cm$^{-1}$ and 1732 cm$^{-1}$.

In an embodiment said complex comprises
 a) Ivacaftor; or a combination of active compounds including Ivacaftor;
 b) a complexing agent which is copolymers of vinylpyrrolidone and vinyl acetate;
 c) and, optionally, poloxamers as a complexing agent; and
 d) sodium lauryl sulfate as an excipient.

In an embodiment, said complex comprises a complexation agent which is a copolymer of vinylpyrrolidone and vinyl acetate; poloxamer 407 or poloxamer 338; and a pharmaceutically acceptable excipient which is sodium lauryl sulfate, in a total amount comprising from about 1.0 weight % to about 95.0 weight % based on the total weight of the complex.

In an embodiment, said complex comprises a complexation agent which is a copolymer of vinylpyrrolidone and vinyl acetate; poloxamer 407 or poloxamer 338; and a pharmaceutically acceptable excipient which is sodium lauryl sulfate, in a total amount comprising from about 50 weight % to about 95 weight % of the total weight of the complex.

In an embodiment, said complex comprises a complexation agent which is a copolymer of vinylpyrrolidone and vinyl acetate and a pharmaceutically acceptable excipient which is sodium lauryl sulfate, in a total amount comprising from about 1.0 weight % to about 95.0 weight % based on the total weight of the complex.

In an embodiment, said complex comprises complexation agent which is a copolymer of vinylpyrrolidone and vinyl acetate and pharmaceutically acceptable excipient which is sodium lauryl sulfate in a total amount comprising from about 50 weight % to about 95 weight % of the total weight of the complex.

Further disclosed herein is a stable complex comprising
 i. 5-40% by weight of Ivacaftor, or a salt or derivative thereof;
 ii. 20-80% by weight of a copolymer of vinylpyrrolidone and vinyl acetate;
 iii. 5-40% by weight of sodium lauryl sulfate; and
 iv. optionally, 0-50% by weight of a poloxamer.

Disclosed herein is a process for the preparation of a stable complex of Ivacaftor, said process comprising the step of mixing a solution of the active agent and at least one complexing agent and optionally one or more pharmaceutically acceptable excipient in a pharmaceutically acceptable solvent with an aqueous solution containing optionally at least one pharmaceutically acceptable excipient.

In an embodiment, said process comprises the step of mixing a solution of Ivacaftor, and at least one complexation agent chosen from copolymers of vinylpyrrolidone and vinylacetate and poloxamers, in a pharmaceutically acceptable solvent with an aqueous solution containing at least one pharmaceutically accepted excipient selected from the group of sodium deoxycolate, dioctyl sodium sulfosuccinate, sodium acetate, cetylpyridinium chloride, citric acid, meglumine and sodium lauryl sulfate.

In an embodiment said complex is obtained via a mixing process.

In an embodiment said complex is obtained via a continuous flow mixing process.

In an embodiment said process is performed in a continuous flow instrument.

In an embodiment said continuous flow instrument is a microfluidic flow instrument.

In an embodiment, said complex is not obtained via a milling process, high pressure homogenization process, encapsulation process and solid dispersion processes.

In an embodiment, said pharmaceutically acceptable solvent is chosen from water, methanol, ethanol, 1-propanol, 2-propanol, acetone, acetonitrile, dimethyl-sulfoxide, tetrahydrofuran, methyl-ethyl ketone or combinations thereof.

In an embodiment, said pharmaceutically acceptable solvent is tetrahydrofuran.

In an embodiment, said pharmaceutically acceptable solvent and said aqueous solvent are miscible with each other.

In an embodiment, said aqueous solvent comprises 0.1 to 99.9% weight of the final solution.

In an embodiment, said aqueous solvent comprises 50 to 90% weight of the final solution.

In an embodiment, said aqueous solvent comprises 50 to 80% weight of the final solution.

In an embodiment, said aqueous solvent comprises 50 to 70% weight of the final solution.

In an embodiment, said aqueous solvent comprises 50 to 60% weight of the final solution.

In an embodiment, said aqueous solvent comprises 45 to 55% weight of the final solution.

In an embodiment, said aqueous solvent comprises 50% weight of the final solution.

In an embodiment, said aqueous solvent comprises 35 to 45% weight of the final solution.

In an embodiment, said aqueous solvent comprises 25 to 35% weight of the final solution.

In an embodiment, said aqueous solvent comprises 15 to 25% weight of the final solution.

In an embodiment, said aqueous solvent comprises 5 to 15% weight of the final solution.

In an embodiment, a pharmaceutical composition comprising the complex together with one or more pharmaceutically acceptable carriers.

In an embodiment, said composition is suitable for oral, pulmonary, rectal, colonic, parenteral, intracisternal, intravaginal, intraperitoneal, ocular, otic, local, buccal, nasal, or topical administration.

In an embodiment, said compositions are suitable for oral administration.

In an embodiment, said composition comprises fast dissolving granules of the complex Ivacaftor formulation.

In an embodiment, said granules are suitable for the preparation of sachet dosage form.

In an embodiment, said complexes are for use in the manufacture of a medicament for the treatment of CFTR mediated diseases.

In an embodiment, said complexes are used for the treatment of CFTR mediated diseases.

CFTR mediated disease is selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington's, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease, Osteoporosis, Osteopenia, bone healing and bone growth (including bone repair, bone regeneration, reducing bone resorption and increasing bone deposition), Gorham's Syndrome, chloride channelopathies such as myotonia congenita (Thomson and Becker forms), Bartter's syndrome type III, Dent's disease, hyperekplexia, epilepsy, lysosomal storage disease, Angelman syndrome, and Primary Ciliary Dyskinesia (PCD), a term for inherited disorders of the structure and/or function of cilia, including PCD with situs inversus (also known as Kartagener syndrome), PCD without situs inversus and ciliary aplasia.

In an embodiment, a method of treatment of CFTR mediated diseases comprises administration of a therapeutically effective amount of complexes or pharmaceutical compositions as described herein.

In an embodiment, a method for reducing the therapeutically effective dosage of Ivacaftor compared to commercially available KALYDECO® comprises oral administration of a pharmaceutical composition as described herein.

In an embodiment, said complexes further comprise one or more additional active agents.

In an embodiment, said additional active agent is Lumacaftor, Tezacaftor or chosen from agents used for the treatment of CFTR mediated diseases.

In an embodiment said complex comprises Ivacaftor; or a combination of active compounds including Ivacaftor; a complexing agent which is a copolymer of vinylpyrrolidone and vinyl acetate and; and sodium lauryl sulfate as an excipient; said complex characterized in that they possess at least one of the following properties:
 a) is instantaneously redispersable in physiological relevant media;
 b) is stable in solid form and in colloid solution and/or dispersion;
 c) has an apparent solubility in water of at least 1 mg/mL;
 d) has a PAMPA permeability of at least $0.4 \times 10^{-6}$ cm/s when dispersed in FaSSIF or FeSSIF biorelevant media, which does not decrease in time at least for 6 month;
 e) exhibits no observable food effect.

In an embodiment, said complex possesses at least two of the properties described in a)-e).

In an embodiment, said complex possesses at least three of the properties described in a)-e).

In an embodiment, said complex further comprises a poloxamer.

The novel complexes possess instantaneous redispersibility, increased apparent solubility and permeability compared to KALYDECO, no observable food effect which deliver the opportunity of precise dosing and ease of administration of the reconstituted complex in solution form.

The expression Ivacaftor is generally used for Ivacaftor, or its salts or its derivatives.

In an embodiment, said complexation agent is chosen from polyethylene glycol glycerides composed of mono-, di- and triglycerides and mono- and diesters of polyethylene glycol, hydroxypropylcellulose, poloxamers (copolymers of ethylene oxide and propylene oxide blocks), copolymer of vinylpyrrolidone and vinyl acetate, poly(2-ethyl-2-oxazoline), polyvinylpyrrolidone, poly(maleic acid/methyl vinyl ether), (polyvinyl caprolactam-polyvinyl acetate-polyethylene glycol graft copolymer, polyoxyl 15 hydroxystearate, ethylene oxide/propylene oxide tetra functional block copolymer, and d-alpha tocopheryl polyethylene glycol 1000 succinate.

In an embodiment, said complexation agents are copolymer of vinylpyrrolidone and vinyl acetate and poloxamer and said pharmaceutically acceptable excipient is sodium lauryl sulfate, and a) is characterized by infrared (ATR) spectrum having characteristic absorption peaks at 588 $cm^{-1}$, 628 $cm^{-1}$, 767 $cm^{-1}$, 842 $cm^{-1}$, 962 $cm^{-1}$, 1019 $cm^{-1}$, 1108 $cm^{-1}$, 1148 $cm^{-1}$, 1240 $cm^{-1}$, 1343 $cm^{-1}$, 1370 $cm^{-1}$, 1425 $cm^{-1}$, 1465 $cm^{-1}$, 1525 $cm^{-1}$, 1567 $cm^{-1}$, 1666 $cm^{-1}$ and 1732 $cm^{-1}$; and b) has characteristic Raman shifts at 552 $cm^{-1}$, 648 $cm^{-1}$, 826 $cm^{-1}$, 845 $cm^{-1}$, 888 $cm^{-1}$, 932 $cm^{-1}$, 1026 $cm^{-1}$, 1062 $cm^{-1}$, 1082 $cm^{-1}$, 1129 $cm^{-1}$, 1140 $cm^{-1}$, 1208 $cm^{-1}$, 1233 $cm^{-1}$, 1262 $cm^{-1}$, 1284 $cm^{-1}$, 1295 $cm^{-1}$, 1361 $cm^{-1}$, 1450 $cm^{-1}$, 1528 $cm^{-1}$, 1573 $cm^{-1}$, 1618 $cm^{-1}$, 1677 $cm^{-1}$, 1738 $cm^{-1}$, 746 $cm^{-1}$, 2884 $cm^{-1}$ and 2936 $cm^{-1}$.

In some embodiments, the compositions may additionally include one or more pharmaceutically acceptable excipients, auxiliary materials, carriers, active agents or combinations thereof.

In some embodiments, active agents may include agents useful for the treatment of CFTR mediated diseases.

In another embodiment, complex formulations of the Ivacaftor with complexation agents and pharmaceutically acceptable excipients in which the complexation agents and pharmaceutically acceptable excipients preferably are associated or interacted with the Ivacaftor, such as the results of a mixing process or a continuous flow mixing process. In some embodiment, the structure of the complex Ivacaftor formulations is different from the core-shell type milled particle, precipitated encapsulated particles, micelles and solid dispersions.

The pharmaceutical composition can be formulated: (a) for administration selected from the group consisting of oral, pulmonary, rectal, colonic, parenteral, intracisternal, intravaginal, intraperitoneal, ocular, otic, local, buccal, nasal, and topical administration; (b) into a dosage form selected from the group consisting of liquid dispersions, gels, aerosols, ointments, creams, lyophilized formulations, tablets, capsules; (c) into a dosage form selected from the group consisting of controlled release formulations, fast melt formulations, delayed release formulations, extended release formulations, pulsatile release formulations, and mixed immediate release and controlled release formulations; or (d) any combination of (a), (b), and (c).

The compositions can be formulated by adding different types of pharmaceutically acceptable excipients for oral administration in solid, liquid, local (powders, ointments or drops), or topical administration, and the like.

In an embodiment, the dosage form is a solid dosage form, although any pharmaceutically acceptable dosage form can be utilized.

Solid dosage forms for oral administration include, but are not limited to, capsules, tablets, pills, powders (sachet), and granules. In such solid dosage forms, the complex formula of Ivacaftor is admixed with at least one of the following: one or more inert excipients (or carriers): (a) fillers or extenders, such as, lactose, sucrose, glucose, mannitol, sorbitol, dextrose, dextrates, dextrin, erythritol, fructose, isomalt, lactitol, maltitol, maltose, maltodextrin, trehalose, xylitol, starches, microcrystalline cellulose, dicalcium phosphate, calcium carbonate, magnesium carbonate, magnesium oxide; (b) sweetening, flavoring, aromatizing and perfuming agents such as saccharin, saccharin sodium, acesulfame potassium, alitame, aspartame, glycine, inulin, neohesperidin dihydrochalcone, neotame, sodium cyclamate, sucralose, tagatose, thaumatin, citric acid, adipic acid, fumaric acid, leucine, malic acid, menthol, propionic acid, tartaric acid; (c) binders, such as cellulose derivatives, acrylic acid derivatives, alginates, gelatin, polyvinylpyrrolidone, starch derivatives, dextrose, dextrates, dextrin, maltose, maltodextrin; (d) disintegrating agents, such as crospovidon, effervescent compositions, croscarmellose sodium and other cellulose derivatives, sodium starch glycolate and other starch derivatives, alginic acid, certain complex silicates and sodium carbonate; (e) solution retarders, such as acrylates, cellulose derivatives, paraffin; (f) absorption accelerators, such as quaternary ammonium compounds; (g) wetting agents, such as polysorbates, cetyl alcohol and glycerol monostearate; (h) lubricants such as talc, stearic acid and its derivatives, solid polyethylene glycols, sodium lauryl sulfate, glyceryl behenate, medium-chain triglycerides or mixtures thereof. For capsules, tablets, and pills, the dosage forms may also comprise buffering agents.

In an embodiment, the dosage form is liquid dispersible granules in a sachet form.

In an embodiment, said liquid dispersible granules comprise the complex formulation of Ivacaftor together with pharmaceutically acceptable excipients selected from the group of fillers or extenders, such as, lactose, sucrose, glucose, mannitol, sorbitol, dextrose, dextrates, dextrin, erythritol, fructose, isomalt, lactitol, maltitol, maltose, maltodextrin, trehalose, xylitol, starches, microcrystalline cellulose, dicalcium phosphate, calcium carbonate, magnesium carbonate, magnesium oxide.

In an embodiment, said liquid dispersible granules comprise the complex formulation of Ivacaftor together with pharmaceutically acceptable excipients selected from the group of sweetening, flavoring, aromatizing and perfuming agents such as saccharin, saccharin sodium, acesulfame potassium, alitame, aspartame, glycine, inulin, neohesperidin dihydrochalcone, neotame, sodium cyclamate, sucralose, tagatose, thaumatin, citric acid, adipic acid, fumaric acid, leucine, malic acid, menthol, propionic acid, tartaric acid.

Further disclosed herein are liquid dispersible granules comprising
a. 25-95% stable complex formulation of Ivacaftor;
b. 5-75% fillers or extenders;
c. 0.5-25% binders;
d. 0.1-5% sweetening, flavoring, aromatizing and perfuming agents;
wherein said liquid dispersible granules disperses within 3 min in liquid; and wherein said liquid dispersible granules obtained by wet or dry processes.

In an embodiment, said dispersion time is between 0.1 min and 10 min.

In an embodiment, said dispersion time is between 0.1 min and 5 min.

In an embodiment, said dispersion time is between 0.1 min and 3 min.

In an embodiment, said dispersion time is between 0.1 min and 1 min.

In an embodiment, said dispersion time is between 0.1 min and 1 min.

In an embodiment, Hausner-ratio of the said liquid dispersible granules of complex Ivacaftor formulations is less than 1.25 more preferably 1.00-1.18

In an embodiment, Hausner-ratio of the said liquid dispersible granules of complex Ivacaftor formulations is between 1.00 and 1.18.

In an embodiment, the particle size (D(90)) of said solid aggregates of complex Ivacaftor formulations is less than 2000 micrometers.

In an embodiment, 60-99% of the said solid aggregates of complex Ivacaftor formulations are in the size range of 160-1200 micrometers In an embodiment, said liquid is water, saliva, other physiologically or biologically acceptable fluid.

In an embodiment, the dosage form is chosen from a tablet and a capsule.

Advantages of the complex Ivacaftor formulations disclosed herein compared to KALYDECO include, but are not limited to (1) physical and chemical stability, (2) instantaneous redispersibility, (3) stability in colloid solution or dispersion in the therapeutic time window, (4) increased apparent solubility and permeability compared to the conventional Ivacaftor formulation, (5) no observable food effect which deliver the opportunity of precise dosing and ease of administration of the reconstituted complex formulation in solution form, (6) good processability.

Beneficial features are as follows: the good/instantaneous redispersibility of solid complex formulations of Ivacaftor in water, biologically relevant media, e.g. physiological saline solution, pH=2.5 HCl solution, FessiF and FassiF media and gastro intestinal fluids and adequate stability in colloid solutions and/or dispersion in the therapeutic time window.

In an embodiment, the complex Ivacaftor formulations have increased apparent solubility and permeability compared to KALYDECO. In some embodiments, the apparent solubility and permeability of the complex Ivacaftor formulae is at least 1 mg/mL and $0.5 \times 10^{-6}$ cm/s, respectively.

In an embodiment, said complex possesses instantaneous redispersibility, has an apparent solubility in water of at least 1 mg/mL, and has a PAMPA permeability of at least $0.5 \times 10^{-6}$ cm/s.

The complexes possess instantaneous redispersibility, increased apparent solubility and permeability compared to KALYDECO, no observable food effect which deliver the opportunity of precise dosing and ease of administration of the reconstituted solid.

The complexes possess instantaneous redispersibility, has a PAMPA permeability of at least $0.4 \times 10^{-6}$ cm/s when dispersed in water, FaSSIF or FeSSIF biorelevant media, which does not decrease in time at least for 6 month, exhibits no observable food effect which deliver the opportunity of precise dosing and ease of administration of the reconstituted complex Ivacaftor in solution form.

BRIEF DESCRIPTION OF THE DRAWINGS

FIG. 1. shows the redispersibility of complex Ivacaftor compositions in ultrapurified water.

FIG. 2. shows the redispersibility and PAMPA permeability of complex Ivacaftor compositions.

FIG. 3. shows the redispersibility and PAMPA permeability of complex Ivacaftor compositions containing vinylpyrrolidone and vinylacetate copolymer (Kollidon VA 64) and poloxamer in different ratios.

FIG. 4. shows the redispersibility and PAMPA permeability of complex Ivacaftor compositions containing vinylpyrrolidone and vinylacetate copolymer (Kollidon VA 64) itself and in combination with different poloxamers.

FIG. 5. shows the physical appearance and stability of the produced complex Ivacaftor formula.

FIG. 6. shows the physical appearance and stability of the produced complex Ivacaftor formula during the flow optimization.

FIG. 7. shows Ivacaftor dissolution from granulated complex Ivacaftor formulation.

FIG. 8. shows the PAMPA permeability of complex Ivacaftor formulation in biorelevant media.

FIG. 9. shows the PAMPA permeability of complex Ivacaftor formulations stored at different condition and measured at different time points.

FIG. 15. shows the comparative apparent solubility data of different Ivacaftor formulations.

FIG. 18. shows the pharmacokinteic parameters following the oral administration of novel complex in the fasted and in the fed state to beagle dogs at 3 mg/kg dose (N=4).

EXAMPLES

Figure 10:
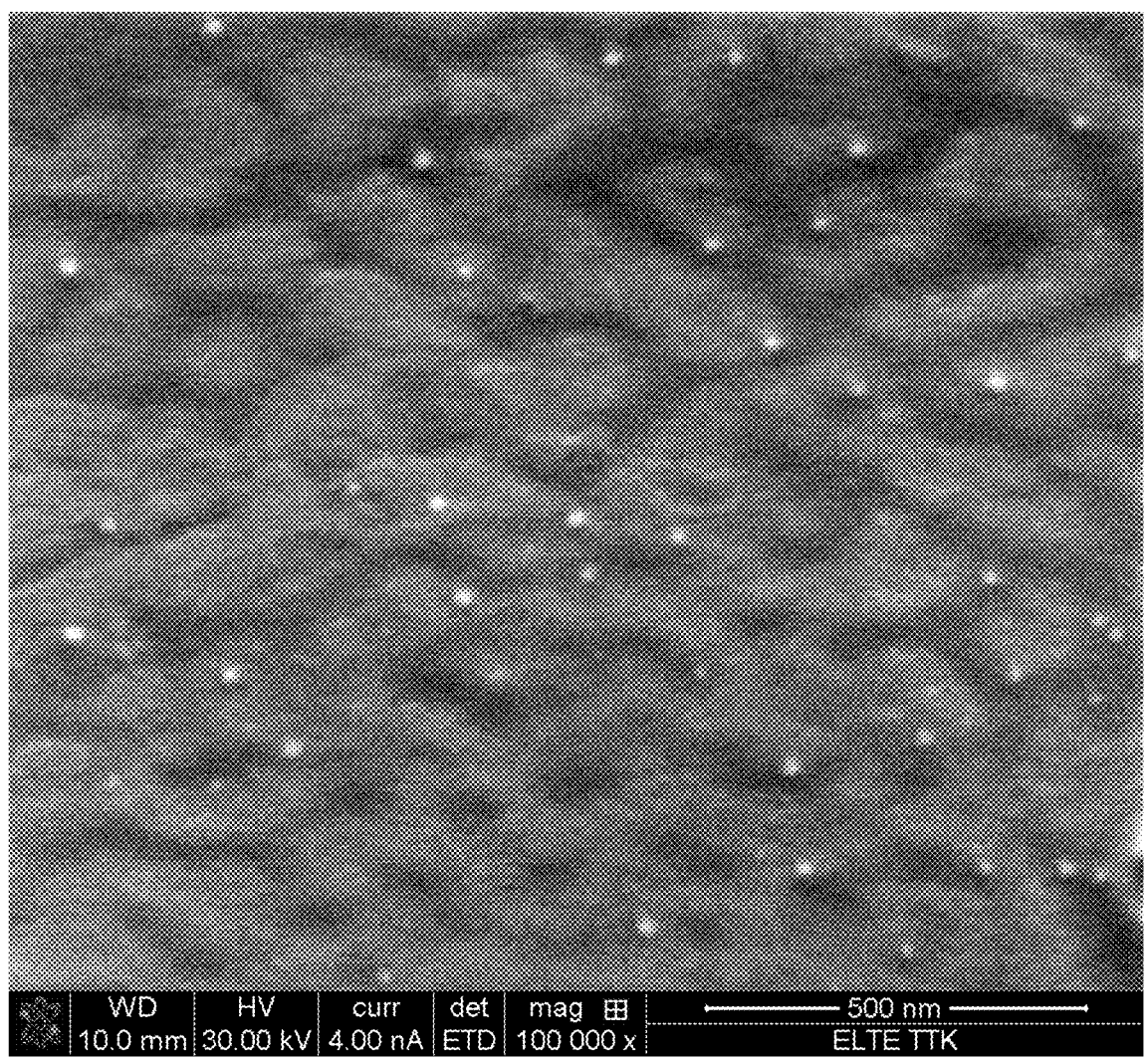
FIG. 10. shows complex Ivacaftor formulation via SEM.

Specific embodiments of the present invention will further be demonstrated by the following examples. It should be understood that these examples are disclosed only by way of illustration and should not be construed as limiting the scope of the present invention.

Selection of Complex Ivacaftor Formulations with Improved Material Properties

Several complexation agents and pharmaceutically acceptable excipients and their combinations were tested in order to select the formulations having instantaneous redispersibility as shown in FIG. 1.

Examples that displayed an acceptable level of redispersibility was selected for further analysis.

PAMPA permeability of the selected formulations was measured in order to select the complex Ivacaftor formulation having the best in-vitro performance (FIG. 2). PAMPA permeability measurements were performed as described by M. Kansi et al. (Journal of medicinal chemistry, 41, (1998) pp 1007) with modifications based on S. Bendels et al (Pharmaceutical research, 23 (2006) pp 2525). Permeability was measured in a 96-well plate assay across an artificial membrane composed of dodecane with 20% soy lecithin supported by a PVDF membrane (Millipore, USA). The receiver compartment was phosphate buffered saline (pH 7.0) supplemented with 1% sodium dodecyl sulfate. The assay was performed at room temperature; incubation time was 4 hours in ultrapurified water, FaSSIF and FeSSIF, respectively. The concentration in the receiver compartment was determined by UV-VIS spectrophotometry (VWR UV-3100PC Scanning Spectrophotometer).

Copolymer of vinylpyrrolidone and vinylacetate (Luviscol VA 64) itself and in combination with poloxamer 338 (Pluronic F108) or poloxamer 407 (Lutrol F127) were selected as complexation agents and sodium lauryl sulfate was selected as pharmaceutically acceptable excipient in order to prepare complex Ivacaftor formulations having improved material characteristics compared to KALYDECO.

Solid complexes of Ivacaftor were prepared by using different ratios of complexation agents and pharmaceutically acceptable excipients (FIG. 3 and FIG. 4).

Production of Complex Ivacaftor Formulations

In order to select the best complex formulation, a solution mixture of Ivacaftor complex formula was prepared. 100 mL Solution 1 was prepared by dissolving 100 mg Ivacaftor and 300 mg copolymer of vinylpyrrolidone and vinylacetate (Kollidon VA 64) and 200 mg poloxamer 338 (Pluronic F108) in 100 mL tetrahydrofurane. The prepared Solution 1 was mixed with Solution 2 containing 25-100 mg sodium lauryl sulfate in 100 mL in order to produce complex Ivacaftor formulation. The appearance and stability of produced colloid solution were monitored. Based on the physical appearance and stability of the produced complex Ivacaftor formula in colloid solution, the best composition was selected for analytical investigations and further work (FIG. 4 and FIG. 5).

In order to select a complex formulation without poloxamer, a solution mixture of Ivacaftor complex formula was prepared. 100 mL Solution 1 was prepared by dissolving 100 mg Ivacaftor and 600 mg copolymer of vinylpyrrolidone and vinylacetate (Kollidon VA 64) in 100 mL tetrahydrofurane. The prepared Solution 1 was mixed with Solution 2 containing 300 mg sodium lauryl sulfate in 100 mL in order to produce complex Ivacaftor formulation. The composition was selected for analytical investigations and further work.

In order to select a complex formulation with poloxamer previously not mentioned, a solution mixture of Ivacaftor complex formula was prepared. 100 mL Solution 1 was prepared by dissolving 100 mg Ivacaftor and 300 mg copolymer of vinylpyrrolidone and vinylacetate (Kollidon VA 64) and 60-200 mg poloxamer 407 (Lutrol F127) in 100 mL tetrahydrofurane. The prepared Solution 1 was mixed with Solution 2 containing 60-100 mg sodium lauryl sulfate in 100 mL in order to produce complex Ivacaftor formulation.

Continuous Flow Production of Complex Ivacaftor Formulations

In order to make the production process industrially feasible, flow production was needed and process intensification was performed by increasing the concentrations of the starting solutions. For the experiments, 1:1 Solvent 1:Solvent 2 ratio was used. A colloid solution of complex Ivacaftor formulation was prepared by mixing process. Solution 1 containing 500 mg Ivacaftor and 1500 mg copolymer of vinylpyrrolidone and vinylacetate (Kollidon VA 64) and 1000 mg poloxamer 338 (Pluronic F108) in 100 mL tetrahydrofuran was mixed with aqueous Solution 2 containing 500 mg sodium lauryl sulfate in 100 mL ultrapurified water in different flow rates. The colloid solution of the complex Ivacaftor formulation was produced at atmospheric pressure and 20-50° C. temperature. The appearance and stability of the produced colloid solution were monitored. Based on the physical appearance and stability of the produced complex Ivacaftor formulation in colloid solution, the best composition was selected for spray-drying experiments. FIG. 6 summarizes the results.

The solidification of the colloid solution was performed by spray-drying technique. 5 mg/mL Ivacaftor, 15 mg/mL copolymer of vinylpyrrolidone and vinylacetate (Kollidon VA 64) and 10 mg/mL poloxamer 338 (Pluronic F108) in tetrahydrofuran and 5 mg/mL sodium lauryl sulfate in water were chosen for starting concentrations. The ratio of the solutions was found to be optimal at 1:1 ratio. The colloid solution of the complex Ivacaftor formulation prepared by the optimal parameter sets was spray-dried (Yamato DL-410/GAS410) in order to obtain solid powder. The best performing production parameters of the spray-drying process were found to be $T_{inlet}$=95° C., $V_{air}$=0.8 m$^3$/min, $M_{in}$=18 mL/min, p=1 bar, $T_{out}$=57-60° C.

The solidification of the colloid solution was performed by spray-drying technique. 5 mg/mL Ivacaftor, 30 mg/mL copolymer of vinylpyrrolidone and vinylacetate (Kollidon VA 64) in tetrahydrofuran and 15 mg/mL sodiumlauryl sulfate in water were chosen for starting concentrations. The ratio of the solutions was found to be optimal at 1:1 ratio. The colloid solution of the complex Ivacaftor formulation prepared by the optimal parameter sets was spray-dried (Yamato DL-410/GAS410) in order to obtain solid powder. The best performing production parameters of the spray-drying process were found to be $T_{inlet}$=95° C., $V_{air}$=0.8 m$^3$/min, $M_{in}$=18 mL/min, p=1 bar, $T_{out}$=55-58° C.

The solidification of the colloid solution was performed by spray-drying technique. 5 mg/mL Ivacaftor, 15 mg/mL copolymer of vinylpyrrolidone and vinylacetate (Kollidon VA 64) and 10 mg/mL poloxamer 407 (Lutrol F127) in tetrahydrofurane and 5 mg/mL sodium lauryl sulfate in water were chosen for starting concentrations. The ratio of the solutions was found to be optimal at 1:1 ratio. The colloid solution of the complex Ivacaftor formulation prepared by the optimal parameter sets was spray-dried (Yamato DL-410/GAS410) in order to obtain solid powder. The best performing production parameters of the spray-drying process were found to be $T_{inlet}$=95° C., $V_{air}$=0.8 m$^3$/min, $M_{in}$=18 mL/min, p=1 bar, $T_{out}$=57-60° C.

The solidification of the colloid solution was performed by spray-drying technique. 5 mg/mL Ivacaftor, 15 mg/mL copolymer of vinylpyrrolidone and vinylacetate (Kollidon VA 64) and 3 mg/mL poloxamer 407 (Lutrol F127) in tetrahydrofurane and 3 mg/mL sodium lauryl sulfate in water were chosen for starting concentrations. The ratio of the solutions was found to be optimal at 1:1 ratio. The colloid solution of the complex Ivacaftor formulation prepared by the optimal parameter sets was spray-dried (Yamato DL-410/GAS410) in order to obtain solid powder. The best performing production parameters of the spray-drying process were found to be $T_{inlet}$=95° C., $V_{air}$=0.85 m³/min, $M_m$=18 mL/min, p=1 bar, $T_{out}$=61° C.

Preparation of Liquid Dispersible Granules Comprising Complex Ivacaftor Formulation Liquid dispersible granules comprising the complex Ivacaftor formulations can be obtained by wet or dry granulation processes.

Dry granulation process includes, but not limited to the slugging or roll compaction of the powder formulation of complex Ivacaftor into compacts and breaking of the compacts into granules with appropriate mesh size. The obtained granules can be blended with excipients chosen from the group consisting of fillers, extenders, binders, disintegrating agents, wetting agents, lubricants, taste masking, sweetening, flavoring, and perfuming agents.

Dry granulation technique can be also applied on the powder blend of complex Ivacaftor formulations. Powder blend consists of the powder formulation of complex Ivacaftor and excipients chosen from the group consisting of fillers, extenders, binders, disintegrating agents, wetting agents, lubricants, taste masking, sweetening, flavoring, and perfuming agents and prepared by blending of the powders. Slugging or roll compaction are used to manufacture compacts from the powder blend. Then the compacts are broken into granules with appropriate mesh size.

Wet granulation process covers the moisturizing of the powder formulations of complex Ivacaftor (direct granulation) or moisturizing the excipients chosen from the group consisting of fillers, extenders, binders, disintegrating agents, wetting agents, lubricants, taste masking, sweetening, flavoring, and perfuming agents with aqueous solution of pharmaceutically acceptable binders and blending it with the powder formulations of complex Ivacaftor (indirect granulation). The particle size of the granules can be controlled by physical impact before and after the drying step.

Liquid dispersible granules of complex Ivacaftor formulation were prepared by compacting appropriate amount of complex Ivacaftor powder blend using 0.5 ton load. The powder blend comprised of the solid formulation of the complex of Ivacaftor and, optionally, sweetening, flavoring, aromatizing and perfuming agents. The height of the compact was found to be optimal between 0.8-1.0 mm. The compacts were broken up by physical impact to form granulates. The particle size of the granules was controlled by sieving with appropriate mesh size to achieve 160-800 micrometers particle size.

Comparative Solubility Tests

The apparent solubility of the granulated complex Ivacaftor formulation containing copolymer of vinylpyrrolidone and vinyl acetate (Kollidon VA 64), poloxamer 338 (Pluronic F108) and sodium-lauryl-sulfate was measured by UV-VIS spectroscopy at room temperature. The solid complex Ivacaftor formulations were dispersed in ultrapurified water in 1-10 mg/mL Ivacaftor equivalent concentration range. The resulting solutions were filtered by 100 nm disposable syringe filter. The Ivacaftor content in the filtrate was measured by UV-Vis spectrophotometry and the apparent solubility was calculated. The filtrate may contain Ivacaftor complex particles which could not be filtrated out using 100 nm pore size filter.

The apparent solubility of complex Ivacaftor formulation containing copolymer of vinylpyrrolidone and vinyl acetate (Kollidon VA 64) and sodium lauryl sulfate and poloxamer 338 was 0.991; 2.356; 4.924 and 9.463 mg/mL, when 1; 2.5; 5; and 10 mg/mL Ivacaftor equivalent formulations were dispersed in ultrapurified water, respectively.

Apparent solubility of complex Ivacaftor formulation containing copolymer of vinylpyrrolidone and vinyl acetate (Kollidon VA 64) and sodium-lauryl-sulfate and poloxamer 338 was 9.463 mg/mL.

The apparent solubility of complex Ivacaftor formulation containing copolymer of vinylpyrrolidone and vinyl acetate (Kollidon VA 64), and sodium lauryl sulfate was measured by UV-VIS spectroscopy at room temperature. The solid complex Ivacaftor formulations were dispersed in ultrapurified water in 1 mg/mL Ivacaftor equivalent concentration range. The resulting solutions were filtered by 100 nm disposable syringe filter. The Ivacaftor content in the filtrate was measured by UV-Vis spectrophotometry and the apparent solubility was calculated. The filtrate may contain Ivacaftor complex particles which could not be filtrated out using 100 nm pore size filter.

The apparent solubility of complex Ivacaftor formulation containing copolymer of vinylpyrrolidone and vinyl acetate (Kollidon VA 64) and sodium lauryl sulfate was 0.936 mg/mL when 1 mg/mL Ivacator equivalent formulation was dispersed in ultrapurified water.

Apparent solubility of complex Ivacaftor formulation containing copolymer of vinylpyrrolidone and vinyl acetate (Kollidon VA 64) and sodium lauryl sulfate was 0.936 mg/mL.

The apparent solubility of complex Ivacaftor formulation containing copolymer of vinylpyrrolidone and vinyl acetate (Kollidon VA 64), poloxamer 407 (Lutrol F127) and sodium lauryl sulfate was measured by UV-VIS spectroscopy at room temperature. The solid complex Ivacaftor formulations were dispersed in ultrapurified water in 1 mg/mL Ivacaftor equivalent concentration range. The resulting solutions were filtered by 100 nm disposable syringe filter. The Ivacaftor content in the filtrate was measured by UV-Vis spectrophotometry and the apparent solubility was calculated. The filtrate may contain Ivacaftor complex particles which could not be filtrated out using 100 nm pore size filter.

The apparent solubility of complex Ivacaftor formulation containing copolymer of vinylpyrrolidone and vinyl acetate (Kollidon VA 64), poloxamer 407 and sodium lauryl sulfate was 0.944 mg/mL when 1 mg/mL Ivacaftor equivalent formulation was dispersed in ultrapurified water.

Apparent solubility of complex Ivacaftor formulation containing copolymer of vinylpyrrolidone and vinyl acetate (Kollidon VA 64), poloxamer 407 and sodium lauryl sulfate was 0.944 mg/mL.

Dissolution Test

Ivacaftor dissolution was measured from the dry granulated formulation of the complex Ivacaftor containing copolymer of vinylpyrrolidone and vinyl acetate (Kollidon VA 64), poloxamer 338 (Pluronic F108) and sodium lauryl sulfate. The dissolution test was performed by dispersing the granulated complex Ivacaftor formulation in purified water at 1 mg/mL concentrations. The dissolved amount was measured with UV-VIS spectrophotometry after filtration with 0.1 μm pore size filter at different time points. Dissolution of Ivacaftor from the granulated complex formulation was instantaneous, within 10 minutes 95% of the Ivacaftor dissolved from the granulated complex Ivacaftor formulation (FIG. 7).

Comparative In-Vitro PAMPA Assays

PAMPA permeabilities of complex Ivacaftor formulations were measured in water, FaSSIF and FeSSIF media and were found to be above $0.4 \times 10^{-6}$ cm/s in all tested media (FIG. 8).

Stability of the Solid Formulation of Complex Ivacaftor

PAMPA permeability of the solid complex Ivacaftor formulations was used to monitor the physical stability of the formulation. PAMPA permeability was measured after storage of the complex Ivacaftor formulation at different conditions. 6 month storage at RT or 40° C. relative humidity showed no significant decrease in the measured PAMPA permeability under any of the conditions tested (FIG. 9).

Structural Analysis

Morphology of complex Ivacaftor formulation containing copolymer of vinylpyrrolidone and vinyl acetate (Kollidon VA 64), poloxamer 338 (Pluronic F108) and sodium lauryl sulfate was investigated using FEI Quanta 3D scanning electron microscope. Complex Ivacaftor formulation comprises spherical particles with particle size less than 50 nm (FIG. 10).

Structural analysis was performed by using Vertex 70 FT-IR with ATR and HORIBA JobinYvon LabRAM HR UV-VIS-NIR instruments.

Figure 11:
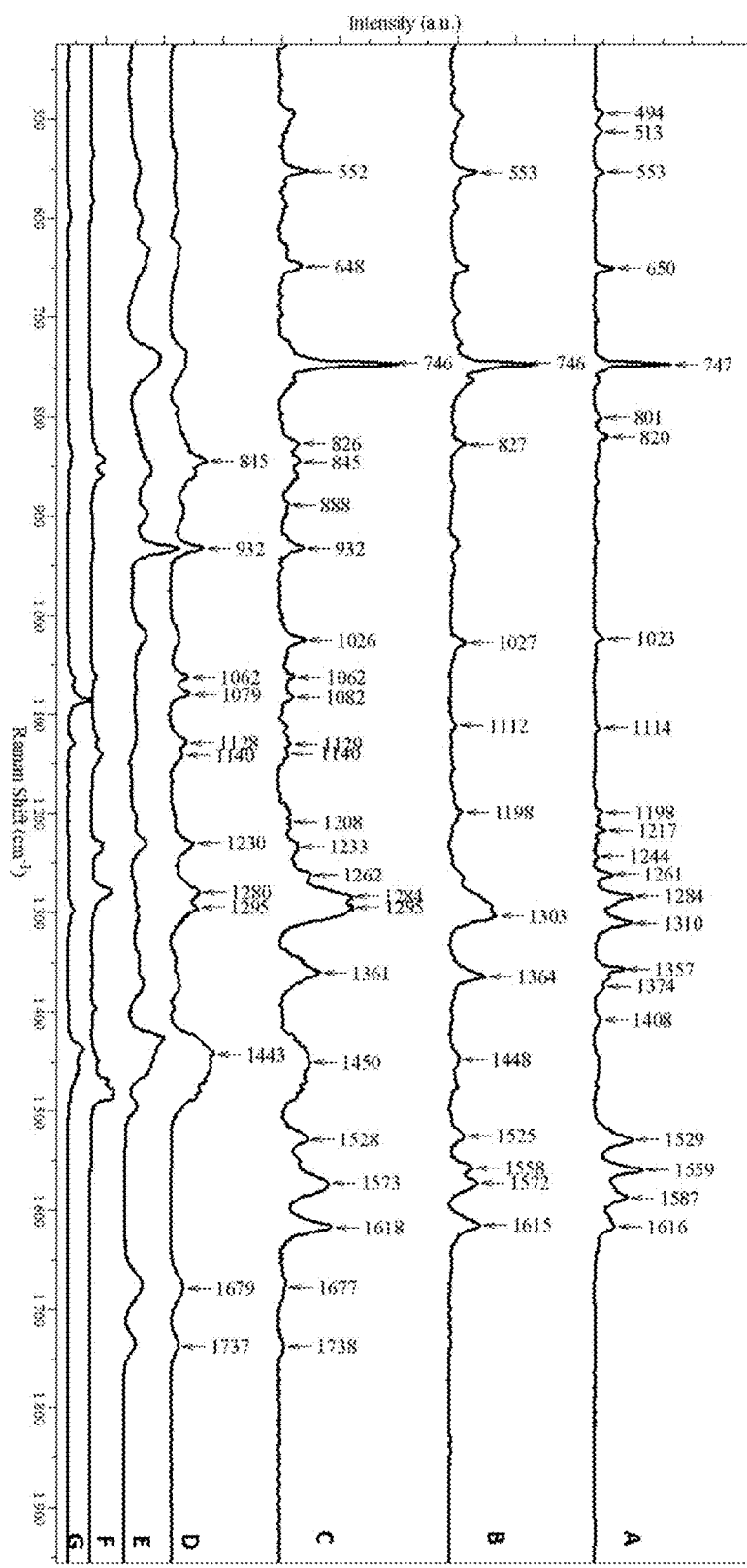
FIG. 11. shows the Raman spectra of crystalline Ivacaftor (A), freeze-dried Ivacaftor (B), complex Ivacaftor formulation (C), placebo sample (prepared in the absence of Ivacaftor) (D), copolymer of vinylpyrrolidone and vinyl acetate (Kollidon VA64) (E), sodium lauryl sulfate (F) and poloxamer 338 (Pluronic F108) (G).
Figure 12:
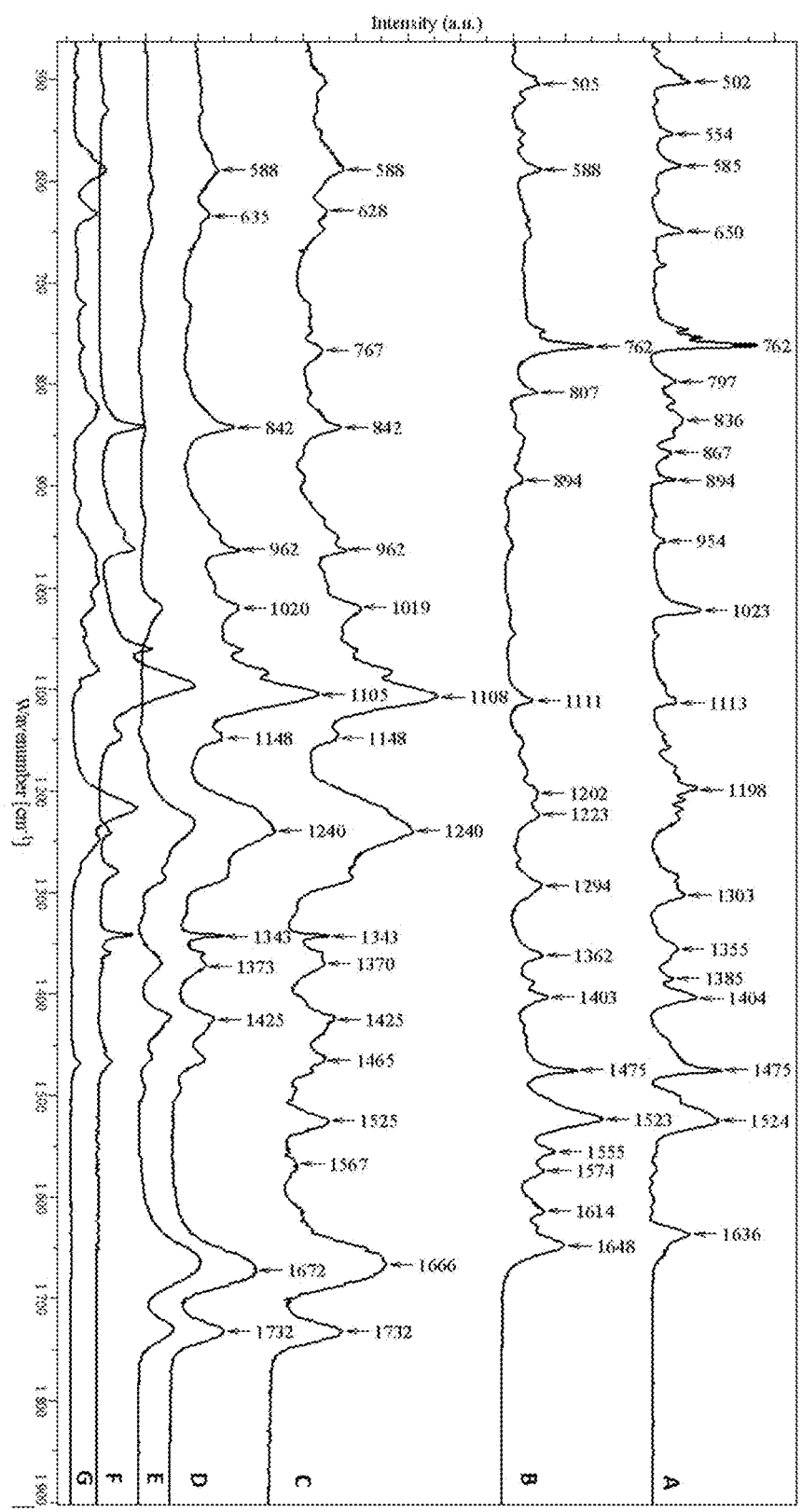
FIG. 12. shows the ATR spectra of crystalline Ivacaftor (A), amorphous Ivacaftor (B), complex Ivacaftor formulation (C), placebo (prepared in the lack of Ivacaftor) (D), copolymer of vinylpyrrolidone and vinyl acetate (Kollidon VA64) (E), sodium lauryl sulfate (F) and poloxamer 338 (Pluronic F108) (G).

Complex Ivacaftor formulation containing copolymer of vinylpyrrolidone and vinyl acetate (Kollidon VA 64), poloxamer 338 (Pluronic F108) and sodium lauryl sulfate or its pharmaceutical composition is characterized by the Raman spectrum shown in FIG. 11 and ATR spectrum shown in FIG. 12.

Complex Ivacaftor formulation containing copolymer of vinylpyrrolidone and vinyl acetate (Kollidon VA 64), poloxamer 338 (Pluronic F108) and sodium lauryl sulfate or its pharmaceutical composition is characterized by Raman shifts at 552 $cm^{-1}$, 648 $cm^{-1}$, 826 $cm^{-1}$, 845 $cm^{-1}$, 888 $cm^{-1}$, 932 $cm^{-1}$, 1026 $cm^{-1}$, 1062 $cm^{-1}$, 1082 $cm^{-1}$, 1129 $cm^{-1}$, 1140 $cm^{-1}$, 1208 $cm^{-1}$, 1233 $cm^{-1}$, 1262 $cm^{-1}$, 1284 $cm^{-1}$, 1295 $cm^{-1}$, 1361 $cm^{-1}$, 1450 $cm^{-1}$, 1528 $cm^{-1}$, 1573 $cm^{-1}$, 1618 $cm^{-1}$, 1677 $cm^{-1}$, 1738 $cm^{-1}$, 746 $cm^{-1}$, 2884 $cm^{-1}$ and 2936 $cm^{-1}$.

Complex Ivacaftor formulation containing copolymer of vinylpyrrolidone and vinyl acetate (Kollidon VA 64), poloxamer 338 (Pluronic F108) and sodium lauryl sulfate or its pharmaceutical composition is characterized by Raman shifts at 1082 $cm^{-1}$, 1233 $cm^{-1}$, 1284 $cm^{-1}$, 1361 $cm^{-1}$, 1528 $cm^{-1}$, 1618 $cm^{-1}$ and 1738 $cm^{-1}$.

Complex Ivacaftor formulation containing copolymer of vinylpyrrolidone and vinyl acetate (Kollidon VA 64), poloxamer 338 (Pluronic F108) and sodium lauryl sulfate or its pharmaceutical composition is characterized by infrared (ATR) spectrum having characteristic peaks at 588 $cm^{-1}$, 628 $cm^{-1}$, 767 $cm^{-1}$, 842 $cm^{-1}$, 962 $cm^{-1}$, 1019 $cm^{-1}$, 1108 $cm^{-1}$, 1148 $cm^{-1}$, 1240 $cm^{-1}$, 1343 $cm^{-1}$, 1370 $cm^{-1}$, 1425 $cm^{-1}$, 1465 $cm^{-1}$, 1525 $cm^{-1}$, 1567 $cm^{-1}$, 1666 $cm^{-1}$ and 1732 $cm^{-1}$.

Complex Ivacaftor formulation containing copolymer of vinylpyrrolidone and vinyl acetate (Kollidon VA 64), poloxamer 338 (Pluronic F108) and sodium lauryl sulfate or its pharmaceutical composition is characterized by ATR spectrum having characteristic peaks at 628 $cm^{-1}$, 767 $cm^{-1}$, 1108 $cm^{-1}$, 1370 $cm^{-1}$, 1465 $cm^{-1}$ and 1666 $cm^{-1}$.

Figure 13:
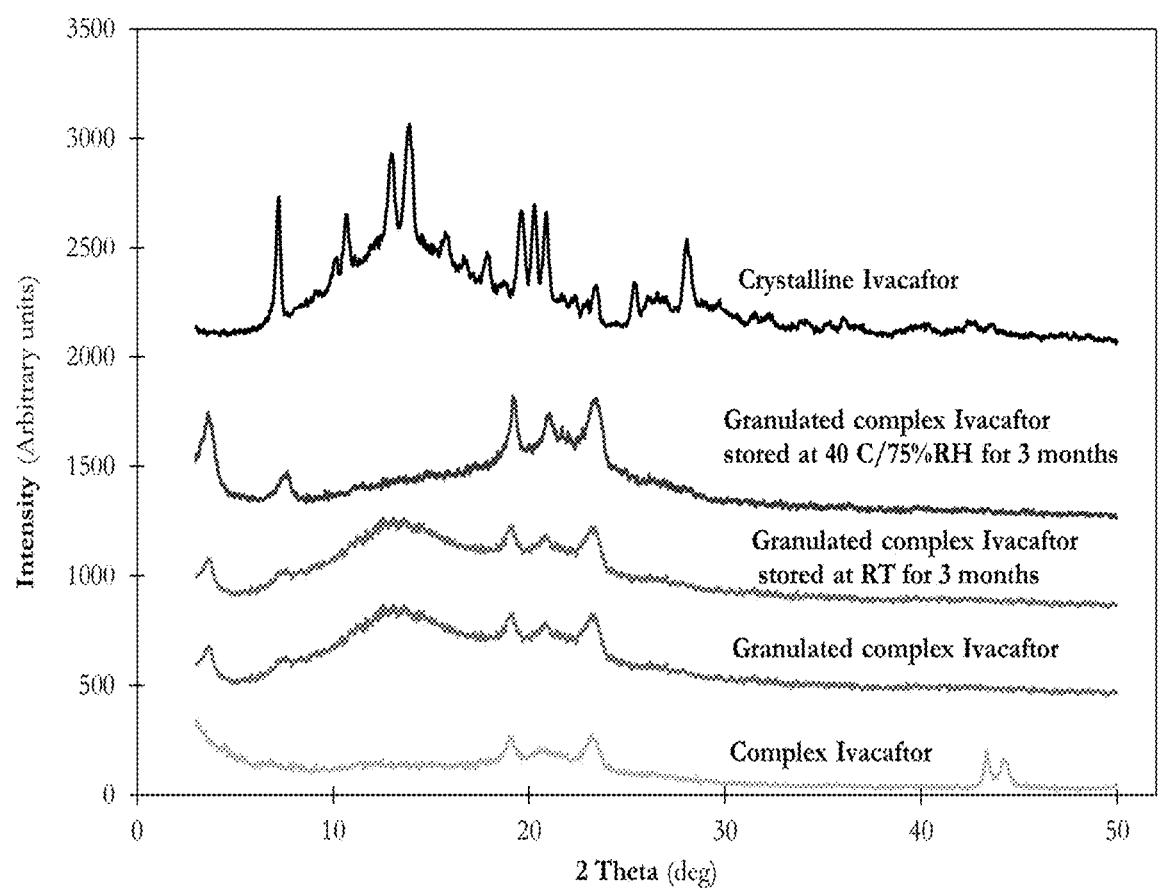
FIG. 13. shows the XRD diffractogram of amorphous Ivacaftor and complex Ivacaftor.

The structure of the complex Ivacaftor formulation containing copolymer of vinylpyrrolidone and vinyl acetate (Kollidon VA 64), poloxamer 338 (Pluronic F108) and sodium lauryl sulfate was investigated by powder X-ray diffraction (XRD) analysis (Philips PW1050/1870 RTG powder-diffractometer). The measurements showed that the Ivacaftor in the complex formulations was XRD amorphous (FIG. 13). Characteristic reflections on the diffractograms of complex Ivacaftor formulation at 43 and 44 2Theta could be attributed to sample holder.

Comparative Formulation Study

Ivacaftor is marketed in its solid dispersion form under the trade name of KALYDECO®. Manufacturing of solid dispersion of Ivacaftor is described in US 20140221424 A1 patent application. Using the manufacturing method described in the patent application, solid dispersion of Ivacaftor was prepared for comparative analytical assays. A solvent system of methyl ethyl ketone (MEK) and water in the ratio of 90 wt % MEK:10 wt % water was heated to 20-30° C. in a reaction vessel equipped with a magnetic stirrer and thermal circuit. Into this solvent system, hypromellose acetate succinate polymer (HPMCAS), sodium lauryl sulfate and Ivacaftor were added in the ratio of 19.5 wt % hypromellose acetate succinate:0.5 wt % SLS:80 wt % Ivacaftor. The resulting mixture was solid formulated by spray-drying method.

Comparative analytical assays were used to investigate the physicochemical properties of the formulation prepared by solid dispersion technology and continuous flow mixing of the present invention.

Figure 14:
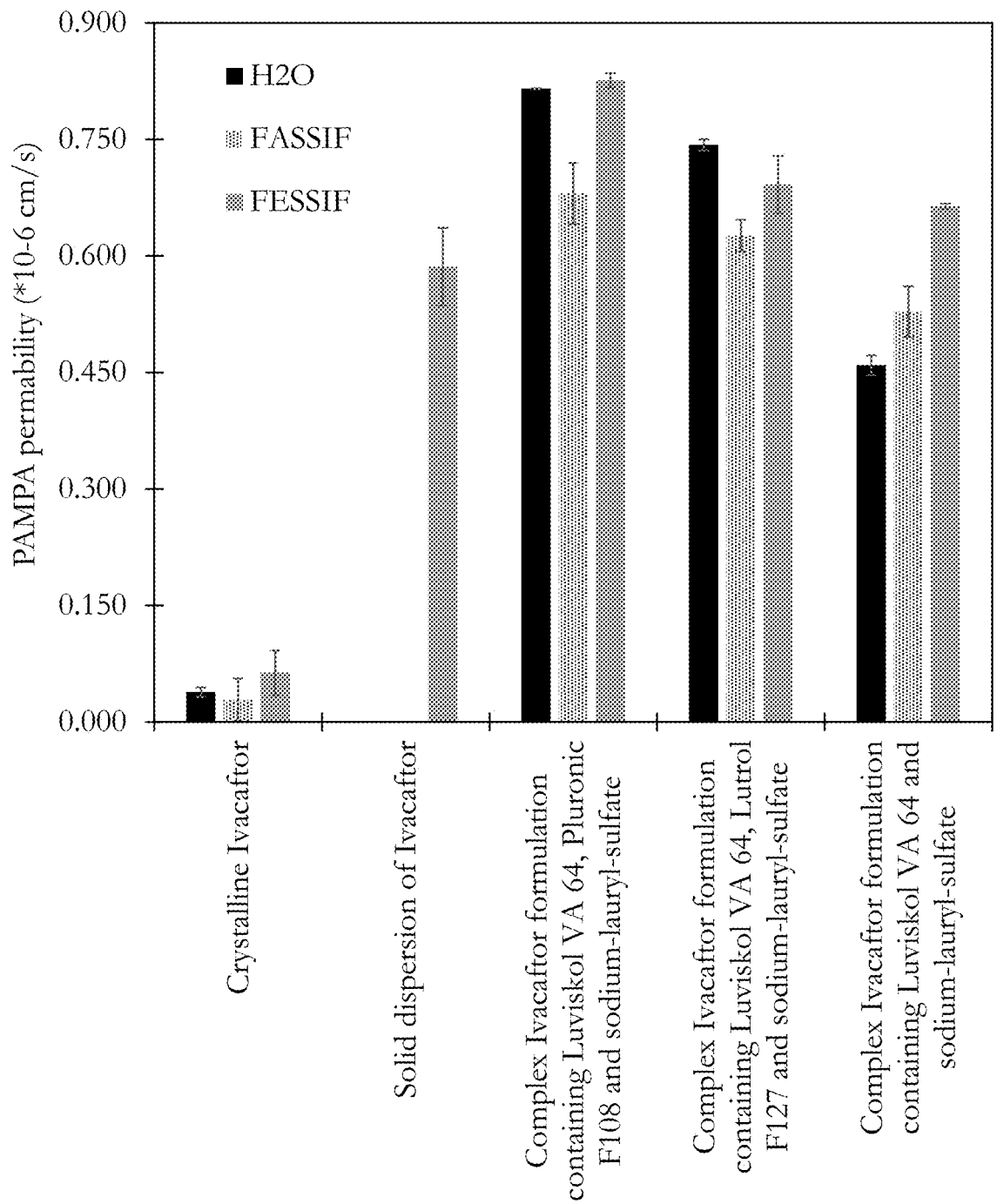
FIG. 14. shows the PAMPA permeability of crystalline Ivacaftor, solid dispersion of Ivacaftor, complex Ivacaftor formulation containing copolymer of vinylpyrrolidone and vinyl acetate (Kollidon VA 64), poloxamer 338 (Pluronic F108) and sodium lauryl sulfate, complex Ivacaftor formulation containing copolymer of vinylpyrrolidone and vinyl acetate (Kollidon VA 64), poloxamer 407 (Lutrol F127) and sodium lauryl sulfate and complex Ivacaftor formulation containing copolymer of vinylpyrrolidone and vinyl acetate (Kollidon VA 64) and sodium lauryl sulfate.

PAMPA permeability of the solid dispersion could not be detected in water FaSSIF, while it was 70% of the permeability of the complex Ivacaftor formulation in FeSSIF (FIG. 14).

Comparative apparent solubility measurements showed that the apparent solubility of complex Ivacaftor formulation was at least 0.9 mg/mL, while apparent solubility of crystalline Ivacaftor, Ivacaftor in physical mixture, amorphous Ivacaftor in aqueous sodium lauryl sulfate solution and solid dispersion was below 0.1 mg/mL (FIG. 15).

Figure 16:
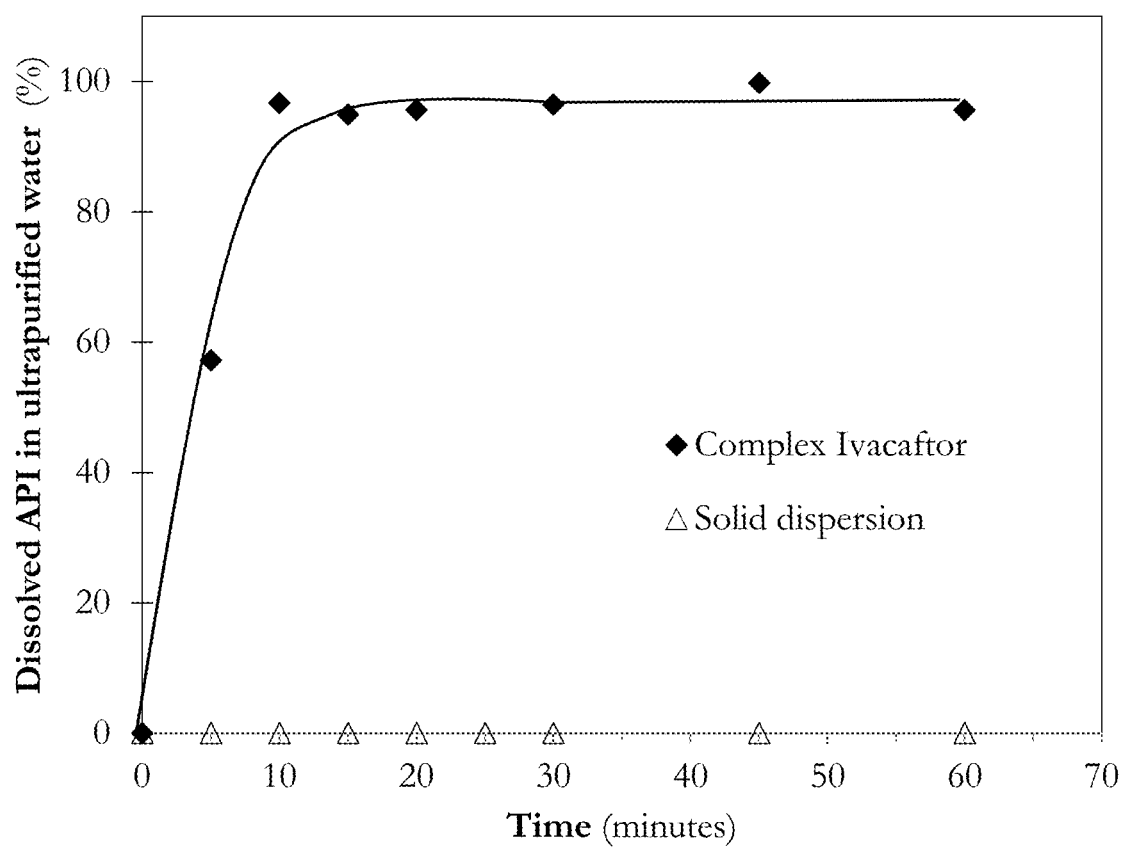
FIG. 16. shows the comparative dissolution tests of solid dispersion of Ivacaftor and complex Ivacaftor formulation.

Comparative dissolution tests performed in water showed that the dissolution of Ivacaftor from the granulated complex formulation containing copolymer of vinylpyrrolidone and vinyl acetate (Kollidon VA 64), poloxamer 338 (Pluronic F108) and sodium lauryl sulfate was instantaneous, within 10 minutes 90% of the Ivacaftor dissolved from the granulated complex Ivacaftor formulation, while 0% Ivacaftor dissolved from the solid dispersion in 60 minutes (FIG. 16).

In-Vivo Pharmacokinetics

In-vivo PK Test in Large Animals

Figure 17:
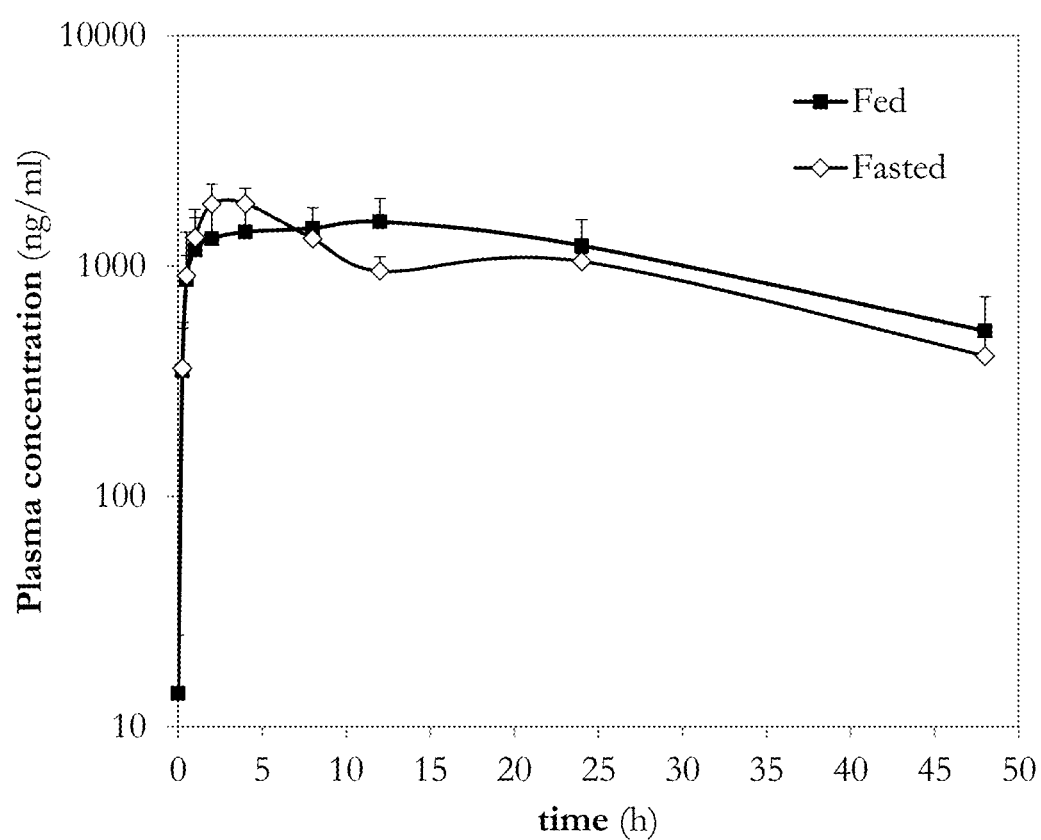
FIG. 17. shows the plasma concentrations of Ivacaftor following the oral administration of novel complex in the fasted and in the fed state to beagle dogs at 3 mg/kg dose (N=4).

A beagle dog study using the granulated complex Ivacaftor formulation containing copolymer of vinylpyrrolidone and vinyl acetate (Kollidon VA 64), poloxamer 338 (Pluronic F108) and sodium lauryl sulfate at a dose of 3 mg/kg was performed in the fasted and fed state. The granulated complex formulation was administered to the animals orally as reconstituted dispersion. Food effect was only 1.1-fold (food effect in humans is 2-4-fold higher in the fed state, that is why the drug has to be taken after a high fat meal). Exposure was 1.25-times higher than the reference exposure. $C_{max}$ was somewhat lower for the complex Ivacaftor formulation, however, for the more important parameter, $C_{24h}$, the complex Ivacaftor was 1.4-times higher (FIG. 17 and FIG. 18).

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of treatment of a cystic fibrosis transmembrane conductance regulator (CFTR) mediated disease in a patient in need thereof, comprising administering to the patient a therapeutically effective amount of a complex comprising:
   a) Ivacaftor, or a salt thereof;
   b) at least one complexing agent which is a copolymer of vinylpyrrolidone and vinyl acetate; and
   c) a pharmaceutically acceptable excipient which is sodium lauryl sulfate;
   wherein said complex has a particle size between 10 nm and 600 nm.

2. The method as recited in claim 1, wherein said complex has a particle size in the range between 10 nm and 400 nm.

3. The method as recited in claim 1, wherein said complex exhibits X-ray amorphous character in the solid form.

4. The method as recited in claim 1, wherein said complex further comprises a poloxamer.

5. The method as recited in claim 1, wherein said complex has an apparent solubility in water of at least 1 mg/mL.

6. The method as recited in claim 1, wherein said complex has a PAMPA permeability of at least $0.5 \times 10^{-6}$ cm/s.

7. The method as recited in claim 1, wherein said complex is suitable for oral, pulmonary, rectal, colonic, parenteral, intracisternal, intravaginal, intraperitoneal, ocular, otic, local, buccal, nasal, or topical administration.

8. The method as recited in claim 1, wherein said complex is suitable for oral administration.

9. The method as recited in claim 1, wherein said complex is administered in solution form.

10. The method as recited in claim 1, wherein said complex is formulated as fast dissolving granules.

11. The method as recited in claim 10, wherein granules are suitable for the preparation of sachet dosage form.

12. The method as recited in claim 1, wherein said CFTR mediated disease is selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington's, spinocerebullar ataxia type I, spinal and bulbar muscular atrophy, dentatorubal pallidoluyisian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease, Osteoporosis, Osteopenia, bone healing and bone growth (including bone repair, bone regeneration, reducing bone resorption and increasing bone deposition), Gorham's Syndrome, chloride channelopathies such as myotonia congenita (Thomson and Becker forms), Bartter's syndrome type III, Dent's disease, hyperekplexia, epilepsy, lysosomal storage disease, Angelman syndrome, and Primary Ciliary Dyskinesia (PCD), a term for inherited disorders of the structure and/or function of cilia, including PCD with situs inversus (also known as Kartagener syndrome), PCD without situs inversus and ciliary aplasia.

13. The method as recited in claim 10, wherein said CFTR mediated disease is selected from cystic fibrosis.

14. The method as recited in claim 1, wherein prior to administering the complex, the method further comprises informing the patient that administration of the complex exhibits no food effect.

* * * * *